United States Patent [19]

Thill

[11] Patent Number: 5,670,630
[45] Date of Patent: Sep. 23, 1997

[54] EXPRESSION OF HEPATITIS B S AND PRES$_2$ PROTEINS IN METHYLOTROPHIC

[75] Inventor: Gregory P. Thill, San Diego, Calif.

[73] Assignee: Research Corporation Technologies, Inc., Tucson, Ariz.

[21] Appl. No.: 467,345

[22] Filed: Jun. 6, 1995

Related U.S. Application Data

[62] Division of Ser. No. 193,714, May 13, 1988, abandoned.

[51] Int. Cl.$^6$ ............................. C07K 14/10; C12N 15/81
[52] U.S. Cl. ..................... 530/403; 530/350; 435/69.3; 435/172.3; 435/254.2; 435/254.23; 435/320.1; 424/189.1
[58] Field of Search ....................... 530/350, 403; 435/69.1, 69.3, 172.3, 320.1, 254.2, 254.23; 536/23.72; 424/189.1

[56] References Cited

U.S. PATENT DOCUMENTS

| 4,816,564 | 3/1989 | Ellis et al. | 530/350 |
| 4,895,800 | 1/1990 | Tschopp et al. | 435/69.3 |

OTHER PUBLICATIONS

Cregg et al. Biotechnology 5:479–485 (1987).
Wood et al. Nature 314:446–449 (1985).

*Primary Examiner*—John L. LeGuyader
*Attorney, Agent, or Firm*—Scully, Scott, Murphy & Presser

[57] ABSTRACT

A process for the enhanced production of antigenic particles consisting essentially of hepatitis B S protein and preS$_2$ protein. Also disclosed are novel DNA molecules and hosts transformed with these molecules.

3 Claims, 10 Drawing Sheets

FIG. I

| RESTRICTION SITES IN AM6 (HBV) | |
|---|---|
| Ava I | 1461 |
| Bam HI | 1398 |
| Bam HI | 26 |
| Bgl II | 1982 |
| Bgl II | 2403 |
| Bgl II | 2427 |
| Bst E II | 2819 |
| Dra I | 829 |
| Dra I | 2180 |
| Hae II | 1435 |
| Hinc II | 215 |
| Hinc II | 959 |
| Hinc II | 1680 |
| Hinc II | 2584 |
| Hinc II | 3115 |
| Hpa II | 1303 |
| Hpa II | 1568 |
| Hpa II | 2328 |
| Pst I | 21 |
| Stu I | 965 |
| Stu I | 1110 |
| Stu I | 1697 |
| Xba I | 245 |

EXPRESSION OF HEPATITIS B S AND PRES$_2$ PROTEINS IN METHYLOTROPHIC

This is a divisional of application Ser. No. 07/193,174, filed on May 13, 1988, now abandoned.

FIELD OF THE INVENTION

This invention relates to the field of recombinant DNA biotechnology. In one aspect, this invention relates to a process for the enhanced expression of antigenic particles consisting essentially of hepatitis B S protein and preS$_2$ protein in methylotrophic yeasts. In another aspect the present invention relates to novel DNA molecules and novel yeast strains transformed therewith.

BACKGROUND

Hepatitis B virus (HBV) causes both acute and chronic diseases and poses a worldwide public health problem. HBV manifests itself as a chronically debilitating infection which can result in progressively severe liver damage, primary carcinoma and death. In the majority of cases, patients completely recover from HBV. However, a significant segment of the population which is infected with HBV becomes chronic carriers of the disease with the potential of transmitting the disease to others.

Recent advances in recombinant DNA techniques have provided many useful methods for elucidating the genetic structure of the HBV, as well as providing the means for preparing vaccines against HBV. The HBV genome is now known to consist of approximately 3.2 kilobase pairs of partially double stranded DNA with a DNA polymerase covalently attached enclosed in a 27 nm nucleocapsid. The nucleocapsid is enveloped in a lipoprotein coat consisting of cellular lipids and hepatitis B surface antigens (HBsAg); this is called the virion and is 42 nm in diameter.

It has also been discovered that the vital coat consists of three different but related surface proteins. These proteins are referred to generally as S, PreS$_2$ and PreS$_1$ proteins. Each virion is comprised of 300–400 S protein molecules and 40–80 preS$_2$ and pre-S$_1$ protein molecules.

The S protein consists of 226 amino acids and is the major component of normal vital lipoprotein coat. The S protein is approximately 24–25 kilodalton (kDa), and may be referred to as P24 or P25. The S protein may also be glycosylated to a 27–28 kilodalton glyco-protein referred to as GP27 or GP28.

The second HBsAg protein is the PreS$_2$ surface antigen, also referred to as the middle HBsAg polypeptide. PreS$_2$ consists of 281 amino acids formed by the addition of 55 amino acids to the N-terminus of the S protein. The PreS2 protein is approximately 31 kilodaltons and may be referred to as the P31 protein. The PreS2 protein also has two glycosylated forms, 33 kilodaltons and 36 kilodaltons, referred to respectively as GP33 and GP36. This antigen is thought to elicit an additional antigenic response in persons who do not respond to S or who respond weakly to S.

The third HBsAg protein is the PreS$_1$ surface antigen, also referred to as the late HBsAg polypeptide. PreS$_1$ consists of between 389–400 amino acids (depending on the antigenic subtype of HBV). The sequence unique to PreS$_1$ consists of 108–119 amino acids which is added to the N-terminus of the complete PreS$_2$ protein. The PreS$_1$ protein is approximately 43 kilodaltons and may also be referred to as the P43 protein. PreS$_1$ also exists in a glycosylated form of 46 kilodaltons designated as GP46 glycoprotein.

In the course of an HBV infection complete vital nucleocapsids are enveloped in a lipoprotein coat, forming 42 nm particles. Also formed during the HBV infection are empty 22 nm particles which consist mostly of the S and preS$_2$ proteins, and some preS$_1$ proteins. While the complete vital nucleocapsid is infectious, the 22 nm empty particles are not infections. The empty particles, however, will elicit an immune response sufficient to confer immunity and may be used in the preparation of vaccines to HBV.

Hepatitis B vaccines prepared with 22 nm particles historically were prepared from the plasma of human carriers of HBV. Unfortunately 22 nm particles derived from human plasma must be extensively purified to remove infectious HBV particles as well as any other plasma-borne pathogens. Additionally the preparation of hepatitis B vaccine bas been severely restricted because of the limited availability of human plasma.

Utilizing recombinant DNA biotechnology, it has been possible to express the hepatitis S protein in a 22 nm particle in transformed for example mammalian cell lines, and *Saccharomyces cerevisiae*. The mammalian systems currently utilized are expensive to use and the Saccharomyces systems produce relatively low yields of S protein.

Efforts to produce the antigenic and potentially more vaccine-effective PreS$_2$ protein have proven unusually difficult. The PreS$_2$ protein has been found to be very susceptible to proteolysis in recombinant systems. Proteolysis yields two smaller protein fragments which may not retain PreS$_2$'s antigenicity. Additionally, the PreS$_2$ protein has been very difficult to express in recombinant systems. The expression level of PreS$_2$ is approximately 1/10th the level of the S protein produced in the same recombinant systems.

It would be a significant contribution to the art to develop an enhanced process for theproduction of antigenic HBV particles containing the S protein and PreS$_2$ protein of HBV. These particles would combine the major S protein with the more potentially antigenic PreS$_2$ protein in a potentially more vaccine-effective form.

Therefore, it is an object of this invention to provide a process for the enhanced production of antigenic HBV particles consisting essentially of S protein and PreS$_2$ protein of HBV.

Yet another object of this invention is to provide novel vectors containing DNA sequences which code for S protein and PreS$_2$ protein.

A further object of this invention is to provide novel methylotrophic yeasts transformed with a vector or vectors capable of enhanced production of the HBV particle consisting of the S protein and an unglycosylated PreS$_2$ protein.

Still another object of this invention is the product produced by the process for the production of antigenic HBV particle consisting essentially of S protein and PreS$_2$ protein.

These and other objects of the invention will become apparent from the disclosure and claims herein provided.

SUMMARY OF THE INVENTION

In accordance with the present invention, I have discovered a process for the enhanced production of an antigenic HBV particle which comprises transforming a methylotrophic yeast with at least one host-compatible expression cassette containing a structural gene for the S protein and at least one vector-compatible expression cassette containing a structural gene for the PreS$_2$ protein and culturing the resultant transformants under conditions suitable to obtain the production of particles.

DETAILED DESCRIPTION OF THE FIGURES

Figure 1:
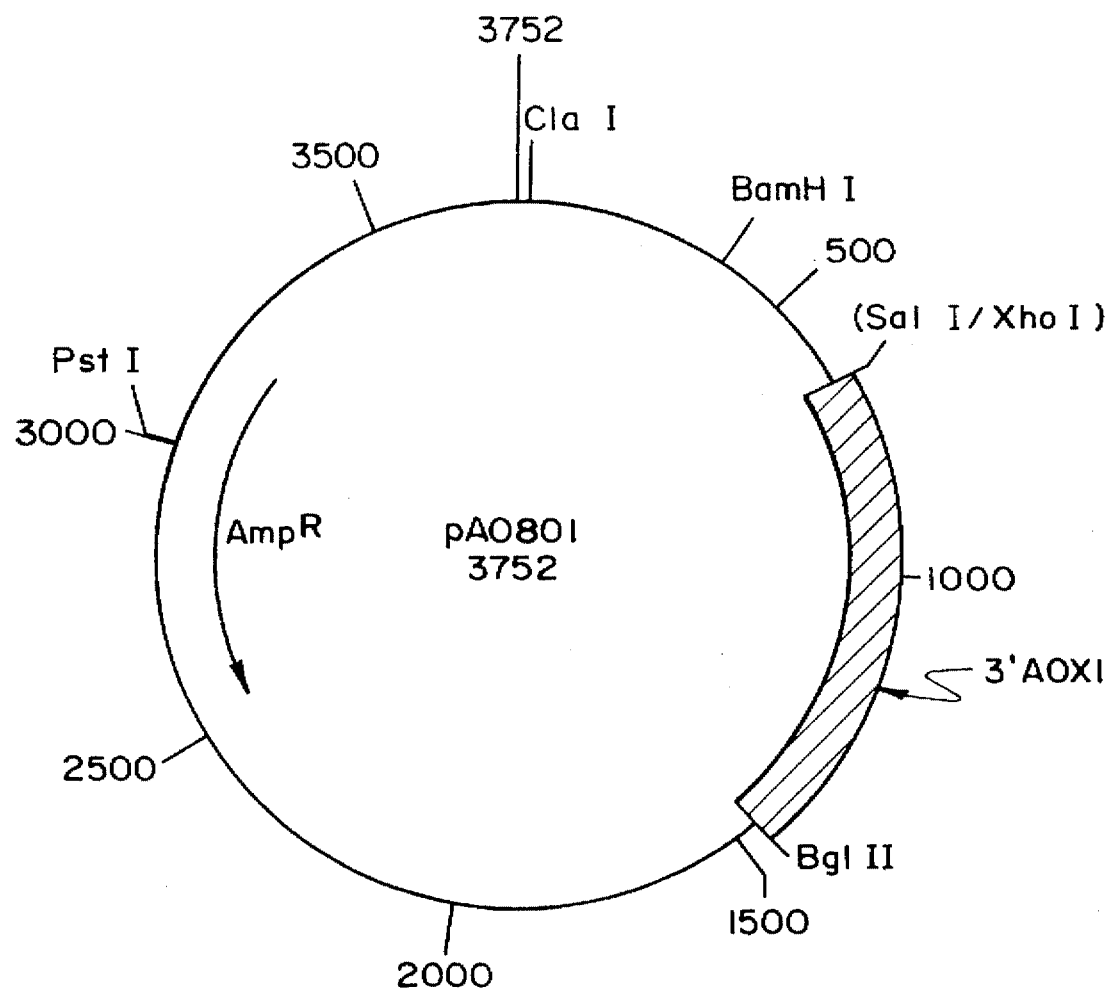

FIG. 1 provides a representation of plasmid pA0801 which is a pBR322-derived plasmid without an EcoRI site at position 1, and which has a BglII site in place of the pBR322 PvuII site, containing a 700 bp BglII/XhoI fragment of the 3' AOX1 termination sequence from pBSAGI5I (NRRL #18021).

Figure 2:
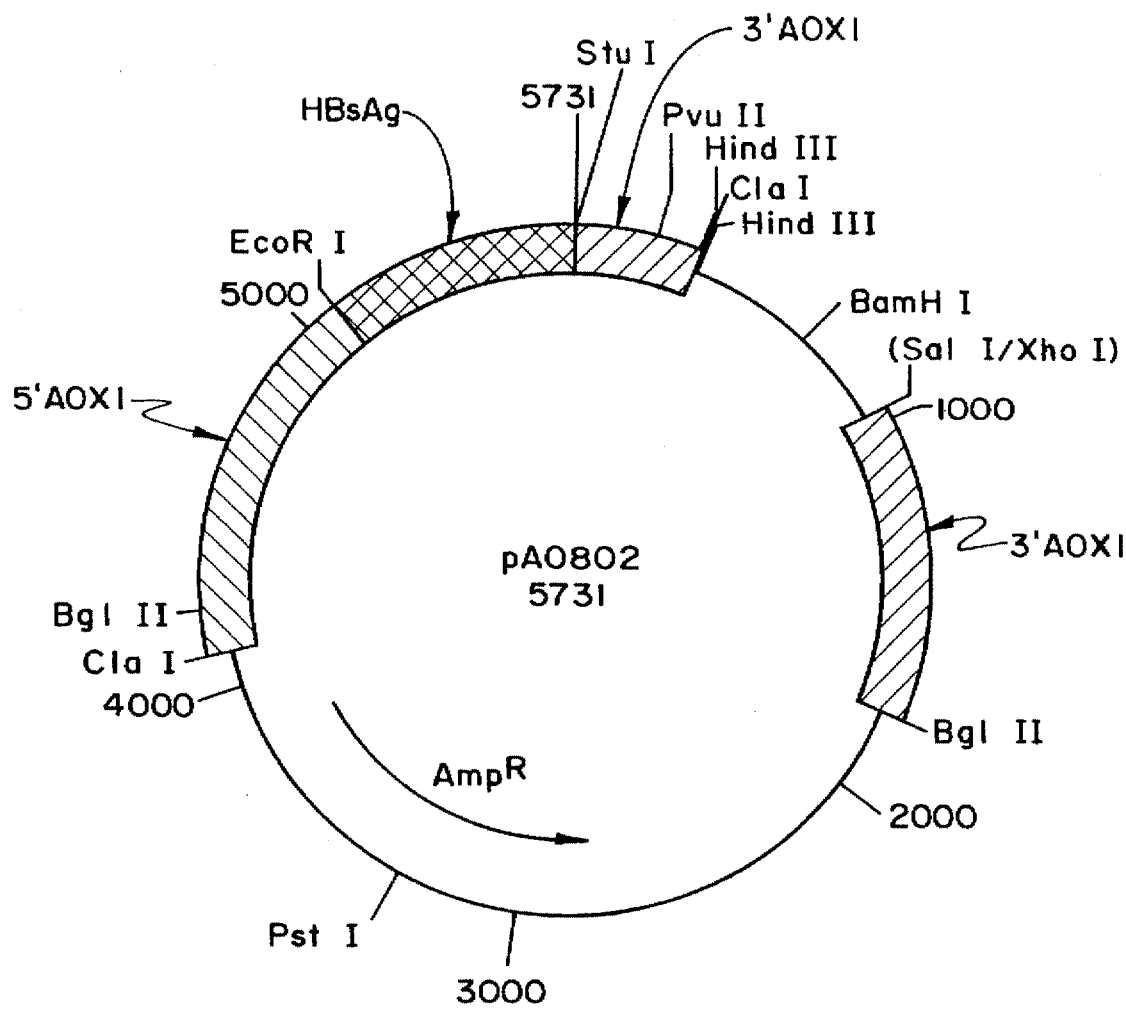

FIG. 2 provides a representation of plasmid pA0802 which is a derivative of plasmid pA0801 containing a promoter-gene-terminator expression cassette from plasmid pBSAGI5I (NRRL #18021) inserted at the ClaI site of plasmid pA0801.

Figure 3:
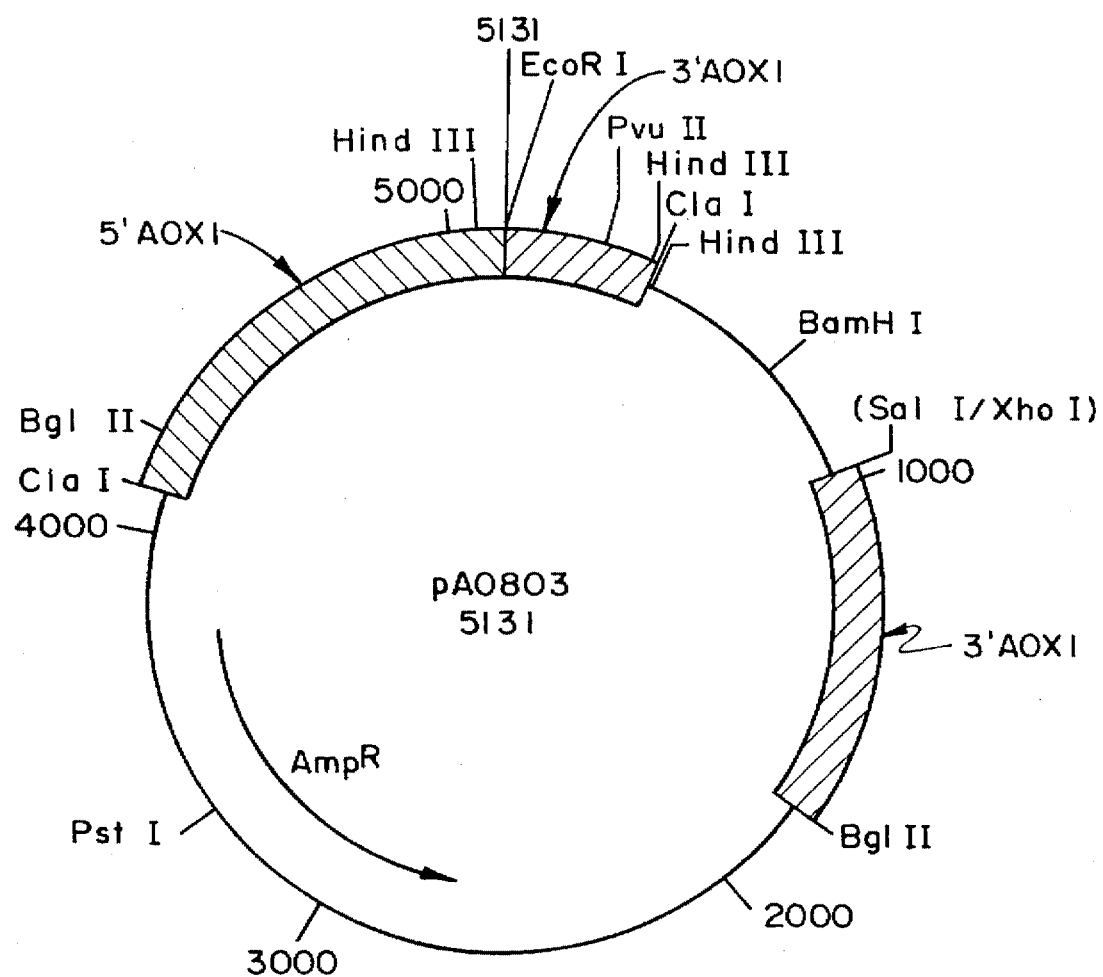

FIG. 3 provides a representation of plasmid pA0803 which is a pA0802 derived plasmid which has had the HBsAg coding sequence removed with a StuI-EcoRI digest and has an EcoRI site inserted at the same site.

Figure 4:
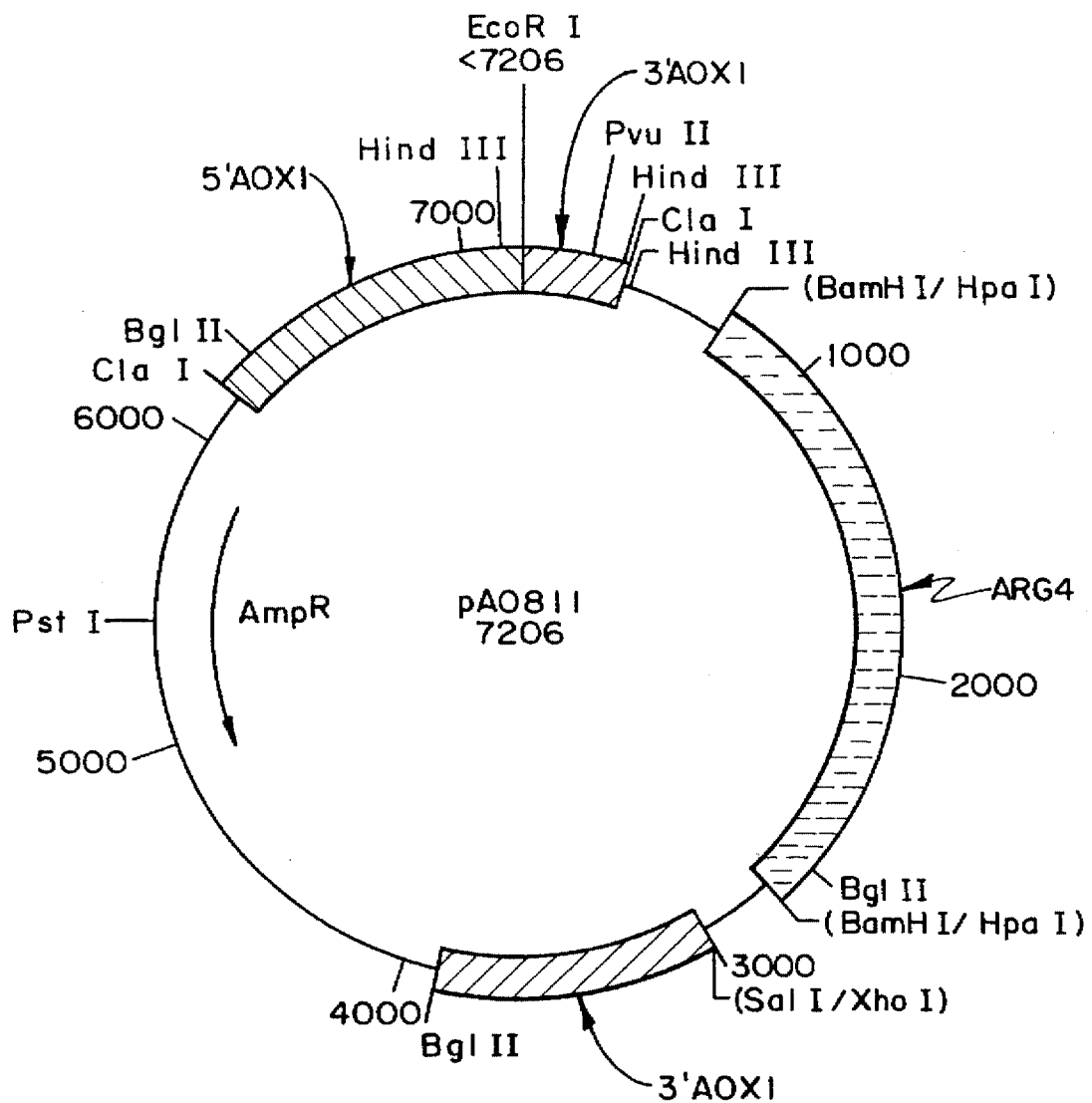

FIG. 4 provides a representation of plasmid pA0811 which was derived from plasmid pA0803, by digesting pA0803 with BamHI and inserting a 2.0 kb fragment containing the Saccharomyces ARG4 gene.

Figure 5A:
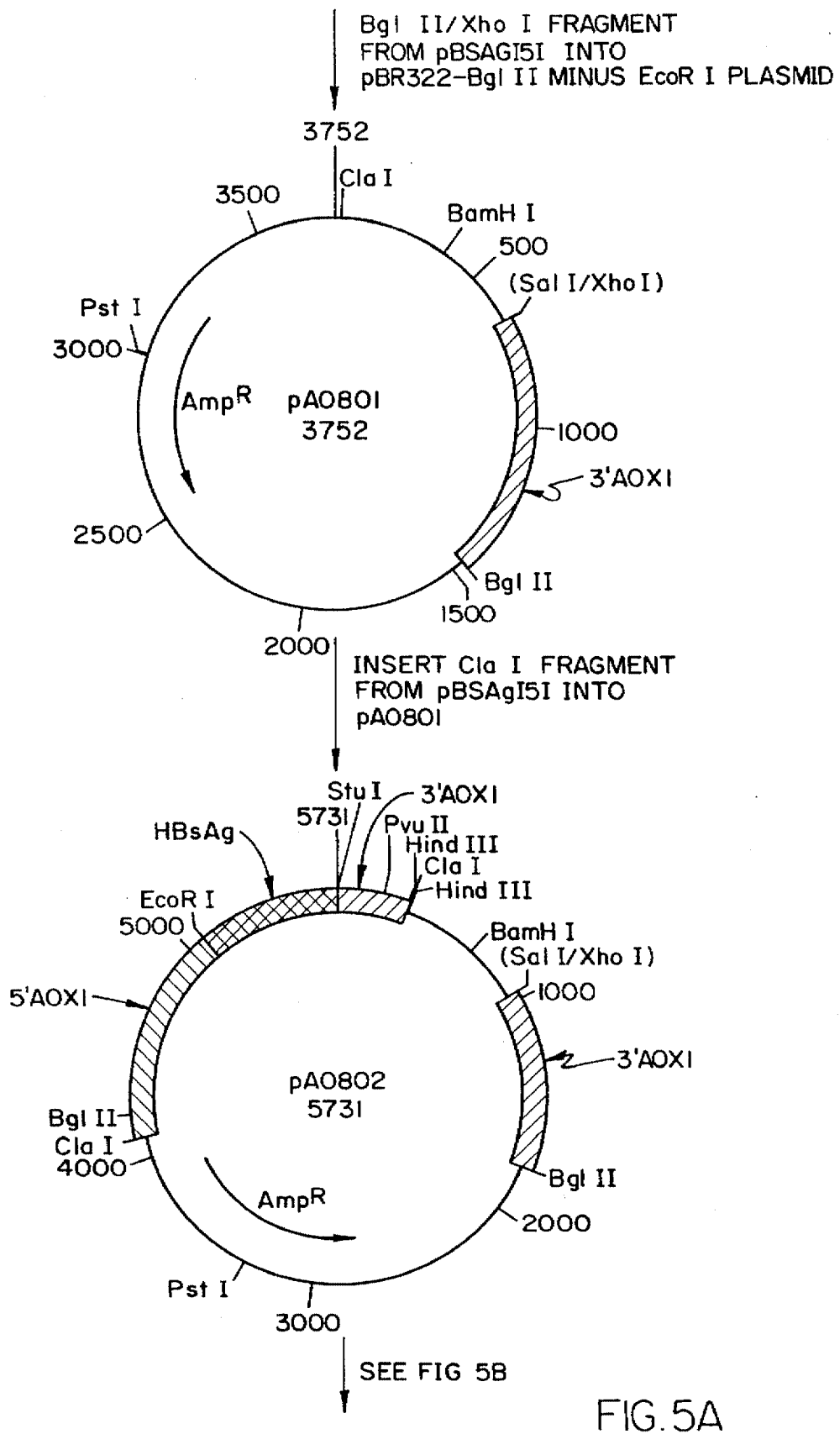

FIG. 5A provides a schematic of the construction of plasmids pA0801 and pA0802.

Figure 5B:
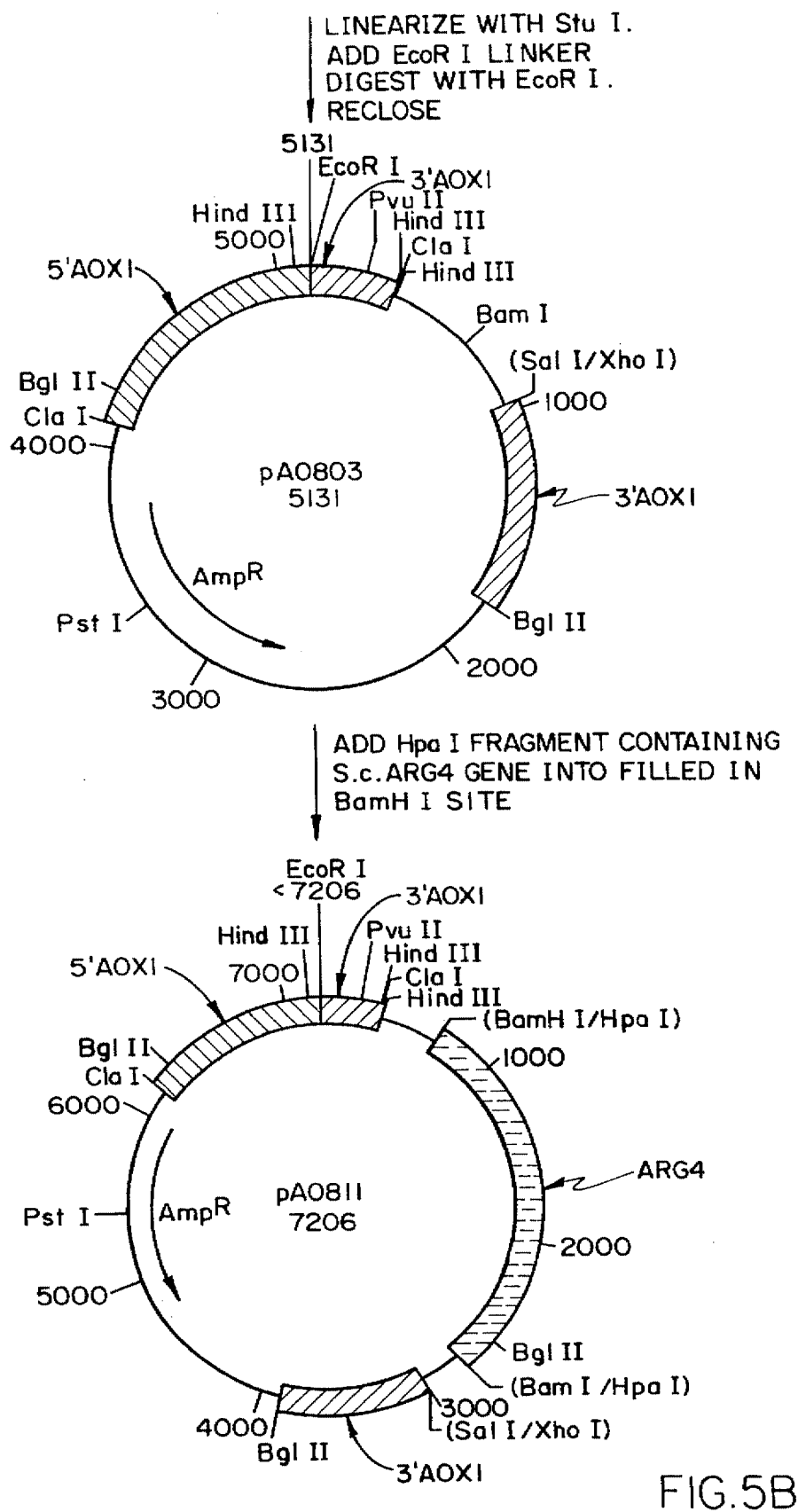

FIG. 5B provides a schematic of the construction of plasmids pA0803 and pA0811.

Figure 6:
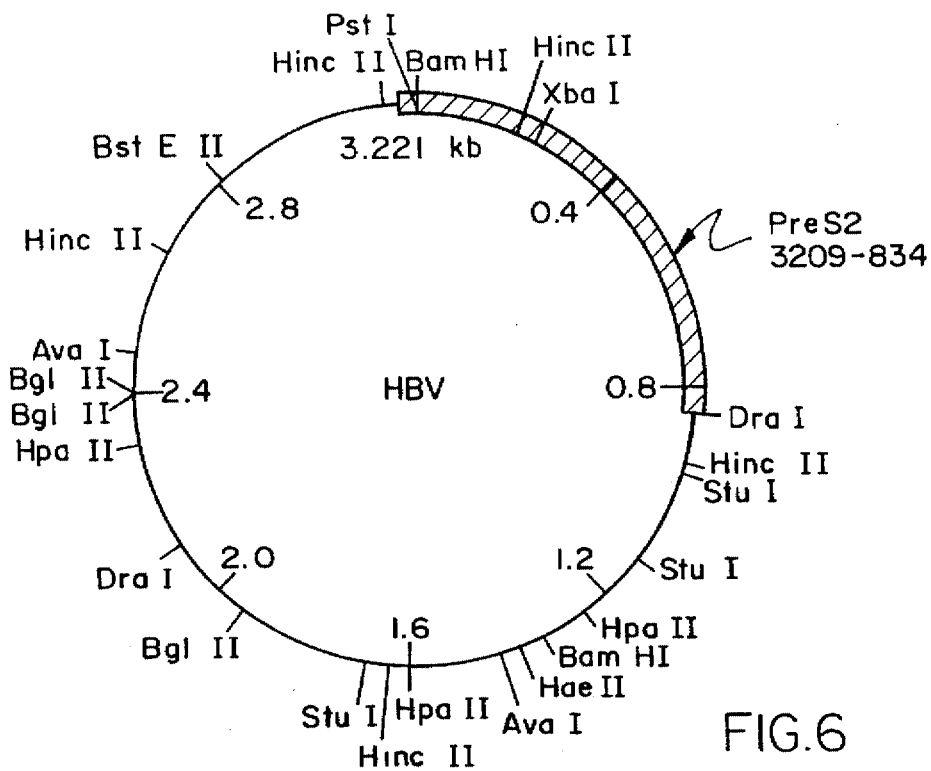

FIG. 6 provides a representation of HBV which contains the $PreS_2$ gene of HBV seratype adw. Plasmid AM6 is a derivative of the HBV genome shown in FIG. 6, wherein the BamHI-digested pBR322 plasmid is inserted at the BamHI site at position 26.

Figure 7:
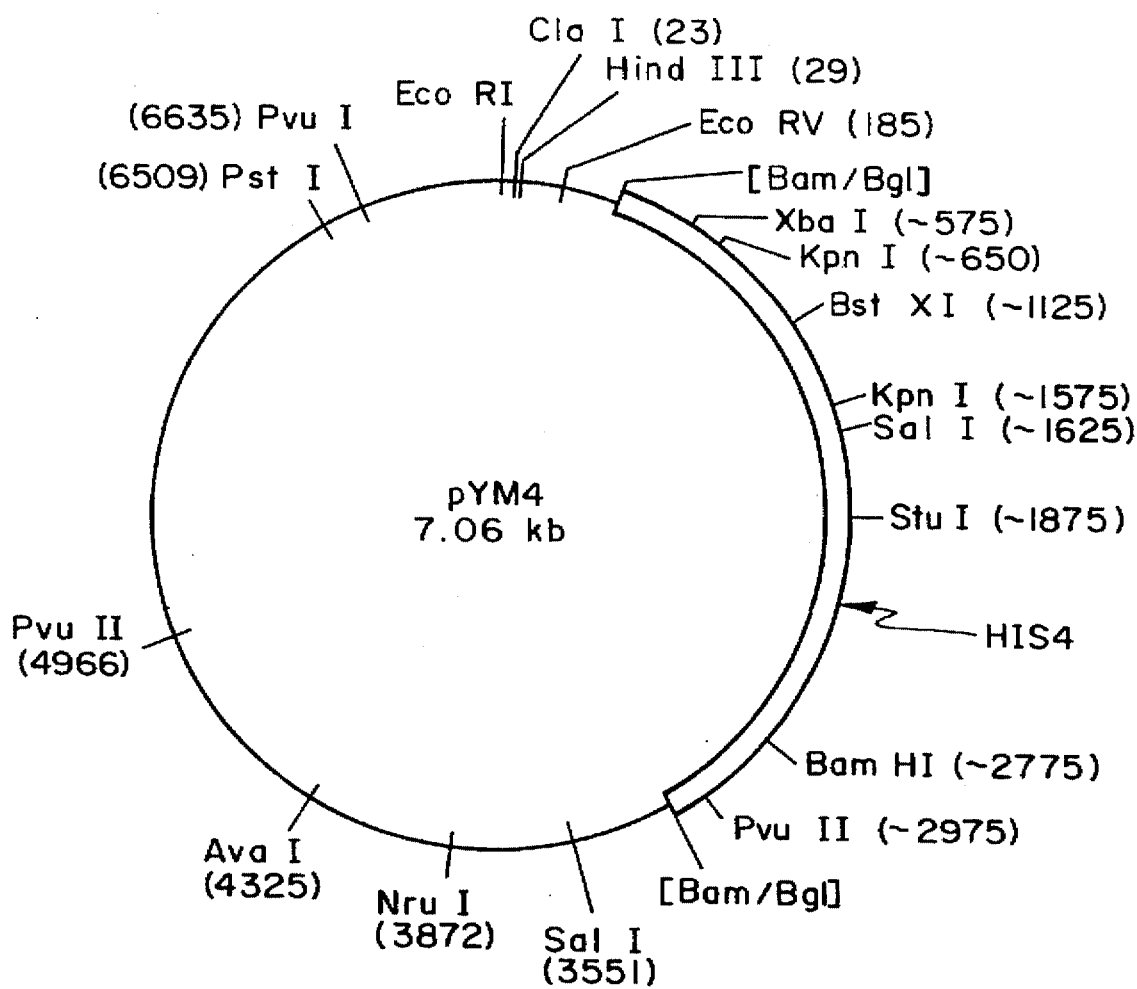

FIG. 7 provides a representation of plasmid pYM4, a pBR322-derived plasmid containing the *Pichia pastoris* HIS4 gene inserted at the BamHI site. Brackets indicate that site was destroyed. The HIS4 gene is on deposit within pYJ30 (NNRL B-15890).

Figure 8:
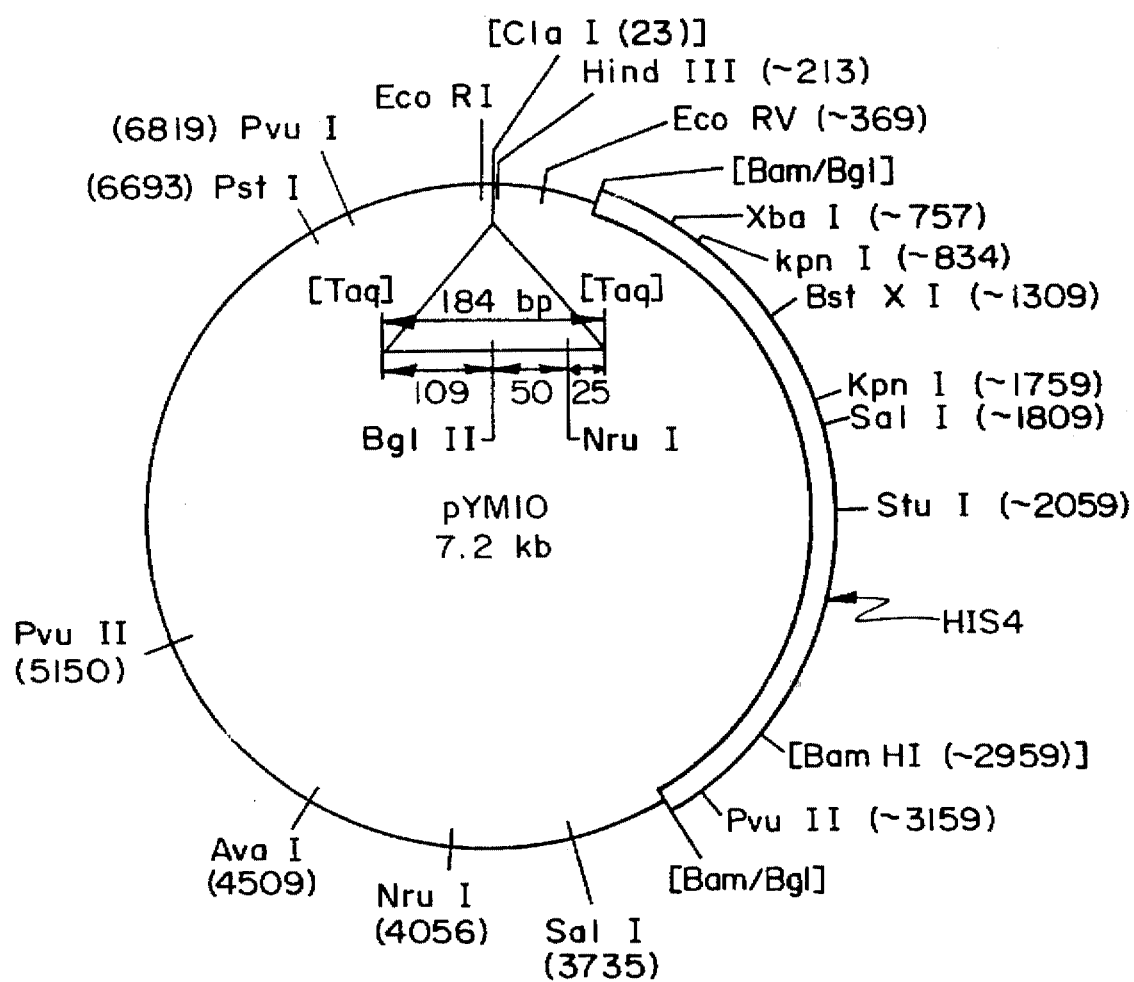

FIG. 8 provides a representation of plasmid pYM10. PYM10 is a derivative of pYJ30 (NRRL B-15890) with the BamHI site at 2959 destroyed. The brackets in the Figure indicate a destroyed restriction site.

Figure 9:
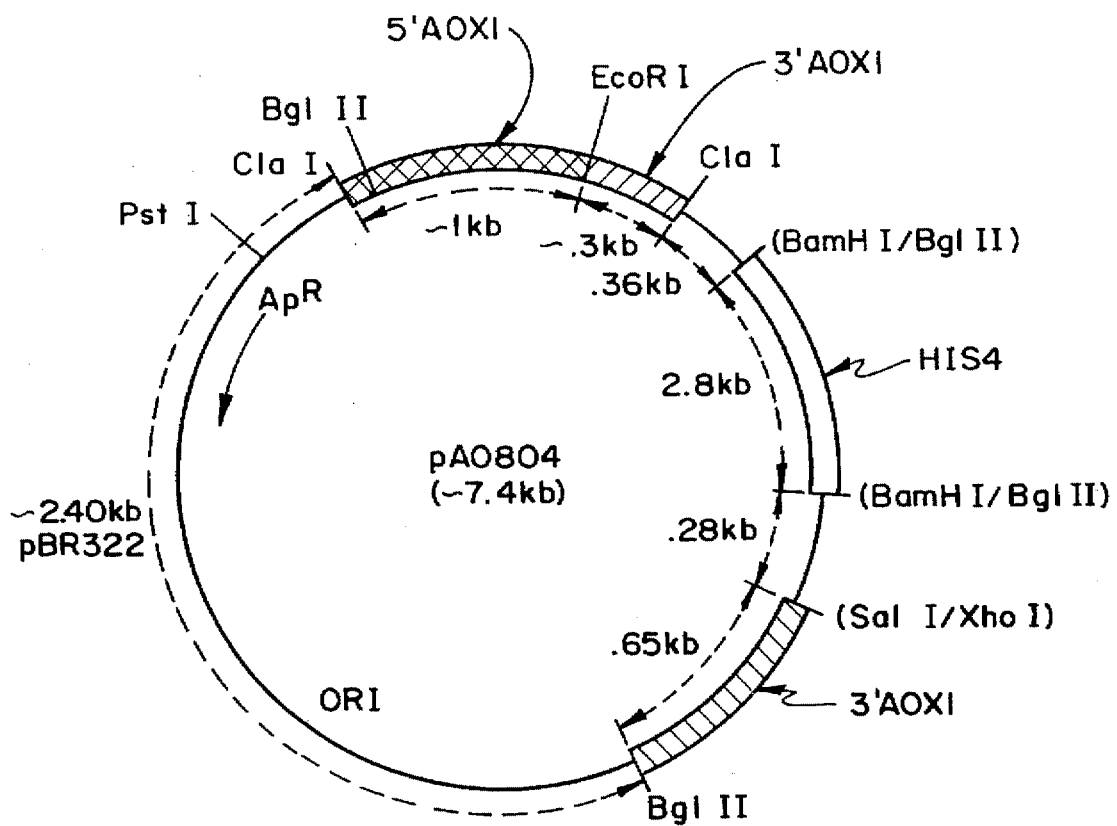

FIG. 9 provides a representation of plasmid pA0804 which contains a linear integrative site-specific vector in the fragment clockwise from BglII to BglII. The structural gene may be inserted in the unique EcoRI site of this plasmid.

DETAILED DESCRIPTION

The $PreS_2$ structural gene is well known in the art and has been sequenced by Lo, *Characteristics of $PreS_2$ Region of Hepatitis B Virus*, 135 Biochemical and Biophysical Research Communications 382 (1986). Numerous workers in this field have cloned this structural gene and expressed it such as Lo, and Valenzuela, *Synthesis and Assembly in Yeast of Hepatitis B Surface Antigen Particles Containing the Polyalbumin Receptor*, 3 Biotechnology 317 (1985) to name only two. The structural gene may thus be obtained from workers in the field, synthesized or reisolated. It is also recognized that any $PreS_2$ seratype may be used for the practice of this invention.

The S structural gene is also well known in the art and has been also sequenced by Lo, supra. The structural gene may be obtained commercially, synthesized or reisolated. It is also recognized that any S seratype may be used for the practice of this invention.

The $PreS_2$ structural gene seratype adw used for one embodiment of this invention was obtained from plasmid AM6. Plasmid AM6 is a derivative of the HBV genome shown in FIG. 6, wherein the pBR322 plasmid is inserted at the BamHI site at position 26. The nucleotide sequence of this $PreS_2$ structural gene is provided in Table 1. The plasmids used herein may be cultured in any suitable *E. coli* host such as MC1061.

Two segments of $PreS_2$ structural genes were recovered from plasmid AM6 and the nucleotide sequence for the first 13 amino acids of the N-terminus was synthesized in vitro. The synthesis of the nucleotide sequence used herein can be accomplished by either chemical or enzymatic means, such as chemical procedures based on phosphotriester, phosphite or cyanoethylphosphoramidite chemistry.

The C-terminus coding region comprising 75% of the structural gene for $PreS_2$ was obtained from plasmid AM6 by a DraI digestion of the plasmid. The DraI digestion was performed using commercially available DraI endonuclease (all endonuclease were used following the manufacturer's recommendation). The DraI fragments were then phenol extracted and ethanol precipitated.

An octameric StuI linker (AAGGCCTT) was then prepared according to standard DNA synthesis techniques and ligated to the DraI fragments using T4 ligase in a blunt end ligation. The ligation was terminated by phenol extraction followed by ethanol precipitation. The resulting fragments were then digested with StuI endonuclease to remove multimers of StuI.

The StuI-linkered fragments were then digested with XbaI. The resultant StuI/XbaI fragment of approximately 600 bp containing the C-terminus coding region of the $PreS_2$ structural gene was isolated by gel electrophoresis.

This 600 bp fragment was then ligated with T4 ligase into a 5 kb XbaI/Stu digest of plasmid pYM4, FIG. 2, which had been isolated agarose gel electrophoresis.

The ligation mixture was then used directly to transform competent *E. coli* cells (MC1061), which were then grown in the presence of ampicillin.

TABLE 1

```
            7   10                  20                  30                  40
         G A A T T C A T G C A G T G G A A C T C C A C T G C C T T C C A C C A A A C T C
                  Start of PreS₂

50                  60                  70                  80
         T G C A G G A T C C C A G A G T C A G G G G T C T G T A T C T T C C T G C T G G 90                 100                 110                120
         T G G C T C C A G T T C A G G A A C A G T A A A C C C T G C T C C G A A T A T T 130                 140                 150                160
         G C C T C T C A C A T C T C G T C A A T C T C C G C G A G G A C T G G G G A C C
```

TABLE 1-continued

```
                170  172          180             190            200
         C T G T G A C G A A C A T G G A G A A C A T C A C A T C A G G A T T C C T A G G
                          Start of S 210             220             230             240
         A C C C C T G C T C G T G T T A C A G G C G G G G T T T T T C T T G T T G A C A 250             260             270             280
         A G A A T C C T C A C A A T A C C G C A G A G T C T A G A C T C G T G G T G G A 290             300             310             320
         C T T C T C T C A A T T T T C T A G G G G G A T C T C C C G T G T G T C T T G G 330             340             350             360
         C C A A A A T C G C A G T C C C C A A C C T C C A A T C A C T C A C C A A C C 370             380             390             400
         T C C T G T C C T C C A A T T T G T C C T G G T T A T C G C T G G A T G T G T C 410             420             430             440
         T G C G G C G T T T T A T C A T A T T C C T C T T C A T C C T G C T G C T A T G 450             460             470             480
         C C T C A T C T T C T T A T T G G T T C T T C T G G A T T A T C A A G G T A T G 490             500             510             520
         T T G C C C G T T T G T C C T C T A A T T C C A G G A T C A A C A A C A A C C A 530             540             550             560
         G T A C G G G A C C A T G C A A A A C C T G C A C G A C T C C T G C T C A A G G 570             580             590             600
         C A A C T C T A T G T T T C C C T C A T G T T G C T G T A C A A A A C C T A C G 610             620             630             640
         G A T G G A A A T T G C A C C T G T A T T C C C A T C C A T C G T C C T G G G 650             660             670             680
         C T T T C G C A A A A T A C C T A T G G G A G T G G G C C T C A G T C C G T T T 690             700             710             720
         C T C T T G G C T C A G T T T A C T A G T G C C A T T T G T T C A G T G G T T C 730             740             750             760
         G T A G G G C T T T C C C C C A C T G T T T G G C T T T C A G C T A T A T G G A 770             780             790             800
         T G A T G T G G T A T T G G G G G C C A A G T C T G T A C A G C A T C G T G A G 810             820             830             840
         T C C C T T T A T A C C G C T G T T A C C A A T T T T C T T T T G T C T C T G G 850  852
         G T A T A C A T T T A A
                          stop codon
```

Successfully transformed colonies were selected and the plasmid DNA extracted by the method of Birnboim and Doly [*Nucleic Acids Research* 7:1513 (1979)]

The extracted plasmid DNA was digested with StuI, phenol extracted and ethanol precipitated. EcoRI linkers were prepared and ligated to the StuI fragments. Excess linkers were removed by EcoRI digestion. These EcoRI linkered fragments were further digested with XbaI and electrophoresed to isolate the fragments containing the C-terminal portion of the preS$_2$ structural gene.

The XbaI-EcoRI digest was ligated into XbaI-EcoRI-cut pUC18. The ligation mixture was transformed into competent *E. coli* cells (MC1061), which was then grown in the presence of ampicillin. Transformed cells containing the C-terminal portion of the preS$_2$ structural gene were selected by fragment digestion analysis employing ClaI and XbaI. The plasmid selected by this process was designated pHS2-B.

The middle portion of the preS$_2$ gene was recovered by first digesting plasmid AM6 with XbaI and BamHI. The desired 250 bp fragment was isolated by gel electrophoresis. The 250 bp XbaI/BamHI fragment was then ligated into pUC18 which had been digested with XbaI and BamHI and used to transform *E. coli* MC1061. Cultures which grew in the presence of ampicillin were analyzed by recovering plasmid DNA and digesting it with BamHI. Those plasmids which contained a 2.7 Kb linear fragment upon electrophoresis were deemed to have the desired 250 bp fragment. One transformed colony containing the 250 bp fragment was isolated and grown on a large scale. The plasmid DNA was isolated and purified from the colony which was digested with EcoRI and BamHI. The vector band was isolated by electrophoresis. The vector was then ligated with the following kinased double stranded oligonucleotide.

```
                    PstI      BamHI
    5' AATTCAATCCGTCTGCAG         3'
    3'     GTTAGGCAGACGTCCTAG     5'
```

The ligation reaction mixture was used to transform E. coli MC1061 and colonies with the correct insert selected by ampicillin resistance. This plasmid was designated pPS2.

The N-terminus coding region of preS$_2$ was prepared as a synthetic oligonucleotide of the following sequence.

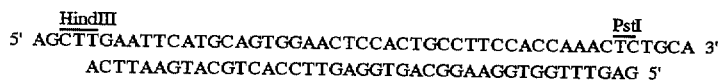

```
       HindIII                                          PstI
5' AGCTTGAATTCATGCAGTGGAACTCCACTGCCTTCCACCAAACTCTGCA 3'
   ACTTAAGTACGTCACCTTGAGGTGACGGAAGGTGGTTTGAG 5'
```

This sequence was cloned into a HindIII and PstI digest of pUC18. The desired transformants were characterized by the presence of an approximately 75 bp fragment after EcoRI digestion and electrophoresis. The plasmids selected by the this method were designated pTBO-2A.

The middle portion of the gene was added by digesting the vector pTBO-2A with PstI and XbaI; the insert was the 250 bp PstI-XbaI fragment from pPS2. Transformants were characterized by the presence of a >300 bp EcoRI fragment as well as 290 bp XbaI/HindIII fragment. The correct isolate was termed pTBO-3. The complete preS$_2$ gene was achieved by inserting the HindIII/XbaI fragment from pTBO-3 into XbaI/HindIII-digested pHS2B. Ampicillin resistant transformants were characterized by the presence of a 825 bp EcoRI fragment. This construct was termed pTBO4.

Culturing the E. coli strain listed above may be accomplished by any suitable means. General techniques for culturing E. coli are already known in the art and any adaptation of these methods to the specific requirements of the strains used herein is well within the abilities of those skilled in the art.

Recovery of plasmid DNA from E. coli can be accomplished by several techniques due to its compact size and closed spherical superhelical form. For example following the harvest, host cells may be pelleted by centrifugation and then resuspended and lysed. The lysate should be centrifuged to remove cell debris and the supernatant containing DNA retained. A phenol extraction can then be performed to remove most other contaminants from the DNA. The phenol-extracted DNA may then be further treated using a density gradient centrifugation or gel filtration technique to separate the plasmid DNA from the bacterial DNA. The techniques for achieving the separation alluded to above are well known in the art and numerous methods of performing these techniques are known.

Nuclease digestion of the plasmid may be accomplished by choosing appropriate endonucleases which will cut the selected plasmid in such a way as to facilitate the recovery of the preS$_2$ structural gene. The endonucleases used will depend on the plasmid from which the preS$_2$ gene is to be excised. For example, the preS$_2$ structural gene contained in plasmid AM6 could be recovered as described in Example I.

Gel electrophoresis of DNA may be accomplished using numerous techniques known in the art such as P. G. Sealy and E. M. Southern, *Gel Electrophoresis of Nucleic Acids—A Practical Approach* (D. Rickwood and B. D. Hames, eds.) p. 39 (1982). Elution may also be accomplished using numerous techniques appropriate for the gel involved, such as electroelution, diffusion, gel dissolution (agarose gels) or physical extrusion (agarose gels). It is additionally recognized that elution may not be necessary with some gels such as high-quality, low melting temperature agarose.

Once the fragment containing the preS$_2$ structural gene or fragments thereof is isolated, additional manipulations may be required before it is inserted in the vector. These manipulations may include, but are not limited to the addition of linkers or blunt-ending the fragment.

For one embodiment of this invention the S gene was constructed from the preS$_2$ gene by M13 mutagenesis. M13 mutagenesis was used to delete the first 165 base pairs (encoding the first 55 amino acids of the preS$_2$ structural gene) resulting in the insertion of an EcoRI site immediately 5' of the ATG start codon for the S structural gene. The techniques for M13 mutagenesis are well known to those skilled in the art, one representative technique which could be used is the technique Zoller and Smith [*Methods in Enzymology* 100:468(1983)]. M13 vectors a the reagents needed for mutagenesis are available from commercial sources such as New England Biolabs.

Mutagenesis as described above was begun by first inserting the preS$_2$ structural gene into the double stranded circular replicative form, or RF, of the M13 vector (for its ease of use, m13mp18 was selected although other H13 vectors could have been used). The preS$_2$ structural gene in plasmid pTB04 was propagated in *E. colid* MC1061, and the plasmid DNA was isolated utilizing the method of Birmboim and Doly, supra. The pTB04 plasmid was then digested with EcoRI. The approximately 825 base pair EcoRI fragment containing the preS$_2$ structural gene was isolated by gel electrophoresis. This fragment was then inserted into the EcoRI site of m13mp18. The ligation mixture was then used to transform competent bacterial cells such as JM101 or JM103. Transformants were selected on the basis of a color reaction which indicated the desired fragment had interrupted the β-galactosidase gene and would form clear instead of blue plaques on indicator plates.

The orientation of the insertion may be determined by sequencing, endonuclease digestion and gel electrophoresis, or any other suitable technique. One clone in which the initiator methionine had been inserted close to the M13 universal primer was isolated and used for the first mutagenesis.

Next, a short oligonucleotide was synthesized in vitro consisting of the following nucleotide sequence:

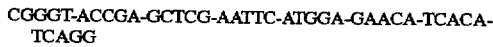

CGGGT-ACCGA-GCTCG-AATTC-ATGGA-GAACA-TCACA-TCAGG

The synthetic sequences used in the practice of this invention may be produced by either enzymatic or chemical means. Suitable means include but are not limited to chemical procedures based on phosphotriester, phosphite or cyanoethylphosphoramidite chemistry.

The single stranded form of N13 with the inserted structural gene was prepared. The synthetic oligonucleotide which is partially complementary to the 5' flanking region of the preS$_2$ gene and the 5' end of the S coding region was then annealed to the single stranded M13 vector containing the preS$_2$ structural gene. Using the partially complementary synthetic oligonucleotide as a primer, DNA synthesis is carried out in vitro with the Klenow fragment and deoxyoligonucleotide triphosphates at 4° C. The partially complementary synthetic oligonucleotide was then extended around the circular H13 template. The reaction six was used to transform competent JM101 or JM103 cells. The transformants were screened by transferring the plaques to nitrocellulose and hybridizing with a radioactively labeled oligonucleotide such that mutant strands hybridized, while the original template did not. These mutants were then used to prepare a template, which was used to transform JM103. These transformants were again screened as before. Positives from the second screening were then sequenced and plaques with the correct sequence were identified. The double stranded replicative form of these colonies was then digested with EcoRI and a 678 base pair fragment was isolated containing the S structural gene. This sequence is provided in Table 2.

single or multiple copies per cell. Included in plasmid DNA is the information required for plasmid reproduction, i.e. an origin of replication is included for bacterial replication. One or more means of phenotypically selecting the plasmid in transformed cells may also be included in the information encoded in the plasmid. Phenotypic or selection markers, such as antibiotic resistance genes or genes which complement defects in the host biochemical pathways, permit clones of the host cells which have been transformed to be recognized, selected, and maintained.

TABLE 2

```
        170 172              180                 190                 200
       G A A T T C A T G G A G A A C A T C A C A T C A G G A T T C C T A G G
              Start S 210                 220                 230                 240
      A C C C C T G C T C G T G T T A C A G G C G G G G T T T T T C T T G T T G A C A 250                 260                 270                 280
      A G A A T C C T C A C A A T A C C G C A G A G T C T A G A C T C G T G G T G G A 290                 300                 310                 320
      C T T C T C T C A A T T T T C T A G G G G G A T C T C C C G T G T G T C T T G G 330                 340                 350                 360
      C C A A A A T T C G C A G T C C C C A A C C T C C A A T C A C T C A C C A A C C 370                 380                 390                 400
      T C C T G T C C T C C A A T T T G T C C T G G T T A T C G C T G G A T G T G T C 410                 420                 430                 440
      T G C G G C G T T T T A T C A T A T T C C T C T T C A T C C T G C T G C T A T G 450                 460                 470                 480
      C C T C A T C T T C T T A T T G G T T C T T C T G G A T T A T C A A G G T A T G 490                 500                 510                 520
      T T G C C C G T T T G T C C T C T A A T T C C A G G A T C A A C A A C A A C C A 530                 540                 550                 560
      G T A C G G G A C C A T G C A A A A C C T G C A C G A C T C C T G C T C A A G G 570                 580                 590                 600
      C A A C T C T A T G T T T C C C T C A T G T T G C T G T A C A A A A C C T A C G 610                 620                 630                 640
      G A T G G A A A T T G C A C C T G T A T T C C C A T C C C A T C G T C C T G G G 650                 660                 670                 680
      C T T T C G C A A A A T A C C T A T G G G A G T G G G C C T C A G T C C G T T T 690                 700                 710                 720
      C T C T T G G C T C A G T T T A C T A G T G C C A T T T G T T C A G T G G T T C 730                 740                 750                 760
      G T A G G G C T T T C C C C C A C T G T T T G G C T T T C A G C T A T A T G G A 770                 780                 790                 800
      T G A T G T G G T A T T G G G G G C C A A G T C T G T A C A G C A T C G T G A G 810                 820                 830                 840
      T C C C T T T A T A C C G C T G T T A C C A A T T T T C T T T T G T C T C T G G 850 852
      G T A T A C A T T T A A
                     stop codon
```

Following the isolation of the S and preS₂ structural genes, the genes are inserted into a suitable methylotrophic yeast vector such as a plasmid or linear site-specific integrative vector. Preferable vectors for the practice of this invention are those compatible with the Pichia genus and most preferably *Pichia pastoris*.

Plasmids have long been one of the basic elements employed in recombinant DNA technology. Plasmids are circular extrachromosomal double-stranded DNA found in microorganisms. Plasmids have been found to occur in To express the preS₂ and the S structural gene in methylotrophic yeast, each gene must be operably linked to a 5' regulatory region and 3' termination sequence, which forms the expression cassette which will be inserted into the host via a vector.

The following terms are defined herein for the purpose of clarification.

Operably linked—refers to a juxtaposition wherein the components a configured so as to perform their function.

Regulatory region—DNA sequences which respond to various stimuli a affect the rate of mRNA transcription.

3' Termination sequence—sequences 3' to the stop codon which function to stabilize the mRNA such as sequences which elicit polyadenylation.

"Host compatible" refers to DNA sequences which will perform their normal function in hosts such as regulatory regions and 3' termination sequences derived from hosts.

Preferred for the practice of the present invention are integrative vectors, such as the linear site-specific integrative vector of Cregg, as described in European Application Serial Number 86114700.7. Such vectors comprise a said arranged sequence of at least 1) a first insertable DNA fragment; 2) a selectable marker gene; and 3) a second insertable DNA fragment.

Insertable DNA fragments are at least about 200 nucleotides in length and have nucleotide sequences which are homologous to portions of the genomic DNA of the host. The various components of the linear site-specific integrative vector are serially arranged forming a linear fragment of DNA such that the expression cassette and the selectable marker gene are positioned between the 3' end of the first insertable DNA fragment and the 5' end of the second insertable DNA fragment. The first and second insertable DNA fragments are oriented with respect to one another in the serially arranged linear fragment as they are so oriented in the parent genome.

Nucleotide sequences useful as the first and second insertable DNA fragments are nucleotide sequences which are homologous with separate portions of the native genomic site at which genomic modification is to occur. Thus, for example, if genomic modification is to occur at the locus of the alcohol oxidase gene, the first and second insertable DNA fragments employed will be sequences homologous with separate portions of the alcohol oxidase gene locus. For genomic modification in accordance with the present invention to occur, the two insertable DNA fragments must be oriented with respect to one another in the linear fragment in the same relative orientation as they exist in the parent genome. Examples of nucleotide sequences which could be used as first and second insertable DNA fragments are nucleotide sequences selected from the group consisting of the alcohol oxidase (AOX1) gene, dihydroxyacetone syntha (DHAS1) gene, p40 gene and HIS4 gene. The AOX1 gene DHAS1 gene, p40 gene and HIS4 gene are disclosed in European application 85113737.2 filed Oct. 29, 1985, incorporated herein by reference.

The first insertable DNA fragment may contain an operable regulatory region which my comprise the regulatory region utilized in the expression cassette. The use of the first insertable DNA fragment as the regulatory region for an expression cassette is a preferred embodiment of this invention. FIG. 4 provides a diagram of a vector utilizing the first insertable DNA fragment as a regulatory region for a cassette.

Optionally as shown in FIG. 9 an insertion site or sites and a termination sequence may be placed immediately 3' to the first insertable fragment. This conformation of the linear site-specific integrative vector has the additional advantage of providing a ready site for insertion of a structural gene without necessitating the addition of a compatible 3' termination sequence.

It is also necessary to include at least one selectable marker gene in the DNA used to transform the host strain. This facilitates selection and isolation of those organisms which have incorporated the transforming DNA. The marker gene confers a phenotypic trait to the transformed organism which the host did not have, e.g., restoration of the ability to produce a specific amino acid where the untransformed host strain has a defect in the specific amino acid biosynthetic pathway or resistance to antibiotics and the like.

Exemplary selectable marker genes may be selected from the group consisting of the HIS4 gene and the ARG4 gene from *Pichia pastoris* and *Saccharomyces cerevisiae*, the invertase gene (SUC2) from *Saccharomyces cerevisiae*, or the neomycin phosphotransferase gene from the *E. coli* transposable elements Tn601 or Tn903.

Those of skill in the art recognize that additional DNA sequences can also be incorporated into the vectors employed in the practice of the present invention, such as for example, bacterial plasmid DNA, bacteriophage DNA, and the like. Such sequences enable the amplification and maintenance of these vectors in bacterial hosts.

If the first insertable DNA fragment does not contain a regulatory region, a suitable regulatory region will need to be inserted operably linked to the structural gene, in order to provide an operable expression cassette. Similarly if no 3' termination sequence is provided at the insertion site to complete the expression cassette, a 3' termination sequence will have to be operably linked to the structural gene to be inserted.

Those skilled in the art are aware of numerous regulatory regions which have been characterized and could be employed in conjunction with methylotrophic yeasts. Exemplary regulatory regions include but are not limited to yeast regulatory regions selected from the group consisting of acid phosphatase, galactokinase, alcohol dehydrogenase, cytochrome c, alpha-mating factor and glyceraldehyde 3-phosphate dehydrogenase regulatory regions isolated from *Saccharomyces cerevisiae*; the primary alcohol oxidase (AOX1), dihydroxyacetone synthase (DHAS1), the p40 regulatory regions, and the HIS4 regulatory region derived from *Pichia pastoris* and the like. Presently preferred regulatory regions employed in the practice of the present invention are those characterized by their ability to respond to methanol-containing media, such regulatory regions selected from the group consisting of AOX1, DHAS1, p40 and disclosed in European Application 85113737.2 filed Oct. 29, 1985.

The most preferred regulatory region for the practice of this invention is the AOX1 regulatory region.

3' termination sequences may be utilized in the expression cassette or be part of the vector as discussed above. 3' termination sequences may function to terminate, polyadenylate and/or stabilize the messenger RNA coded for by the structural gene when operably linked to a gene. A few examples of illustrative sources for 3' termination sequences for the practice of this invention include but are not limited to the *Saccharomyces cerevisiae, Hansenula polymorpha*, and Pichia 3' termination sequences. Preferred are those derived from *Pichia pastoris* such as those selected from the group consisting of the 3' termination sequences of AOX1 gene, DHAS1 gene, p40 gene and HIS4 gene. Particularly preferred is the 3' termination sequence of the AOX1 gene.

Those of skill in the art recognize that additional DNA sequences can also be incorporated into the vectors employed in the practice of the present invention, such as for example, bacterial plasmid DNA, bacteriophage DNA, and the like. Such sequences enable the amplification and maintenance of these vectors in bacterial hosts.

Another suitable vector would be an integrative vector which would comprise an arranged sequence of at least 1) an insertable DNA fragment, 2) a selectable marker gene, 3) an expression cassette and optionally 4) another insertable DNA fragment. The components of the integrative vector are equivalent to those used in the linear integrative site-specific vector except there needs to be only one insertable DNA fragment, however integrative vectors are believed to integrate the entire vector by homologous recombination. Preferred are circular integrative vectors such as is shown in FIG. 4. For the practice of the current invention it is currently preferred to use linear transformation vectors such as the BglII fragments of the constructs shown in FIG. 9 and the circular form of the integrative vector in FIG. 4.

The insertion of a S or preS$_2$ structural gene into suitable vectors may be accomplished by any suitable technique which cleaves the vector chosen at an appropriate site or sites and results in at least one operable expression cassette containing a S or preS$_2$ structural gene being present in the vector.

Ligation of a S or preS$_2$ structural gene may be accomplished by any appropriate ligation technique such as utilizing T4 DNA ligase.

The initial selection, propagation, and optional amplification of the ligation mixture of a S or preS$_2$ structural gene and a vector is preferably performed by transforming the mixture into a bacterial host such as E. coli. Suitable transformation techniques for E. coli are well known in the art. Additionally, selection markers and bacterial origins of replication necessary for the maintenance of a vector in a bacterial host are also well known in the art.

The isolation and/or purification of the desired plasmid containing a S or preS$_2$ structural gene in an expression system may be accomplished by any suitable means for the separation of plasmid DNA from the host DNA.

Similarly the vectors formed by ligation may be tested preferably after propagation to verify the presence of a S or preS$_2$ gene and its operable linkage to a regulatory region and a 3' termination sequence. This may be accomplished by a variety of techniques including but not limited to endonuclease digestion, gel electrophoresis, or endonuclease digestion-Southern hybridization.

For the practice of this invention at least two different compatible expression cassettes must be transformed into the host cell. There are several methods by which these two different expression cassettes may be inserted into the host such as placing two functional expression cassettes in a vector (vital, plasmid or linear site-specific integrative) and transforming a host with these vectors. Another method of transforming a host with at least two different expression cassettes (S and preS$_2$), would be to transform the host with two different vectors, one containing the S expression cassette and the other containing the preS$_2$ expression cassette. The transformation with two different vectors (dual transformation) could be accomplished by simultaneous transformation (both vectors present in a single transformation event) or sequentially (one vector transformed into the host followed by a second transformation with the other vector in to the previously transformed host cells). Dual sequential transformation is currently the preferred method of transformation.

Transformation of plasmids or linear vectors into yeast hosts may be accomplished by suitable transformation techniques including but not limited to those taught by Hinnen et al, Proc. Natl. Acad. Sci. 75, (1978) 1929; Ito et al, J. Bacteriol 153, (1983) 163; Cregg et al Mol. Cell Biol. 5 (1985) pg. 3376; or Sreekrishna et al, Gene, 59 (1987) pg. 115. Preferable for the practice of this invention is the transformation technique of Cregg. It is desirable in one embodiment of this invention to utilize an excess of linear vectors and select for multiple insertions by Southern hybridization.

The yeast host for transformation may be any suitable methylotrophic yeast. Methylotrophic yeast include but are not limited to yeast capable of growth on methanol selected from the genera consisting of Hansenula, Candida, Kloeckera, Pichia, Saccharomyces, Torulopsis and Rhodotorula. A list of specific species which are exemplary of this class of yeasts may be found in C. Anthony, The Biochemistry of Methylotrophs, 269 (1982). Presently preferred are methylotrophic yeasts of the genus Pichia such as the auxotrophic Pichia pastoris GS115 (NRRL Y-15851) or PPF1 (NRRL-Y-18017). Auxotrophic methylotrophic yeasts are also advantageous to the practice of this invention for their ease of selection. It is recognized that wild type methylotrophic yeast strains may be employed with equal success if a suitable transforming marker gene is selected, such as the use of SUC2 to transform Pichia pastoris to a strain capable of growth on sucrose or an antibiotic resistance marker is employed, such as G418$^R$ gene.

For the practice of the current invention it is currently preferred to use the two selection markers in combination, to select for the stable transformation of S and preS$_2$ into the host. Thus it is advantageous for the practice of the invention to use host and vector combinations which assure that when two different selection markers are used in two different vectors each marker may be independently selected for. One such host and vector combination would be the use of PPF1 (HIS4, ARG4) with vectors pA0804 (HIS4 marker) and pA0811 (ARG4 marker). Another possible combination would be the use of an auxotroph defective in only one pathway in combination with a gene which is complementary to the defect and an antibotic resistance gene or a gene which generates a new phenotype such as SUC2.

Transformed methylotrophic yeast cells can be selected for using appropriate techniques including but not limited to culturing previously auxotrophic cells after transformation in the absence of a biochemical product required (due to the cell's auxotrophy), selection by the detection of a new phenotype ("methanol slow"), or culturing in the presence of an antibiotic which is toxic to the yeast in the absence of a resistance gene contained in the transformant.

Isolated transformed methylotrophic yeast cells are cultured by appropriate fermentation techniques such as shake flask fermentation, high density fermentation or the techniques disclosed by Cregg et al, High-Level Expression and Efficient Assembly of Hepatitis B Surface Antigen in the Methylotrophic Yeast, Pichia Pastoris, 5 Bio/Technology 479 (1987).

Expression may be accomplished by methods appropriate to the regulatory region employed. Preferably if methanol responsive regulatory regions are utilized, the induction of expression may be accomplished by exposing the transformed cells in a nutrient media to an appropriate alcohol for the regulatory region employed.

The antigenic particles may be recovered in a crude form by lysing transformed cells which have been induced for a sufficient period, using standard techniques such as bead milling, followed by centrifugation sufficient to remove cellular debris. Those of skill in the art are aware of numerous methods available for the extraction of a heterologous protein from unicellular host organisms which could be substituted for the general extraction technique above or for further purification. The preferred method of purification for the practice of this invention is disclosed in an application filed April 13, 1988 by Cregg et al., attorney docket number 32342US incorporated herein by reference.

The following non-limiting examples are provided to further illustrate the practice of this invention.

EXAMPLES

General information pertinent to the Examples:

Strains

*Pichia pastoris* GS115 (his4) NRRL Y-15851 was the host yeast strain used in these examples.

*Pichia pastoris* PPF1 (arg4 his4) NRRL Y-18017.

*E. coli* MC1061 NRRL 18016.

*E. coli* JM103 delta (lac pro) thi rpsL (strA) supE endA sbcB hsdR.

Media

| | |
|---|---|
| YPD, 1 liter | 20 g yeast extract |
| | 20 g peptone |
| | 20 g dextrose |
| LB broth, 1 liter | 5.0 g yeast extract (Difco) |
| | 10.0 g tryptone (Difco) |
| | 5.0 g NaCl |
| TE buffer | 1.0 mM EDTA |
| | in 0.01M (pH 7.4) Tris buffer |
| PEG Solution | 20% polyethylene glycol-3350 |
| | 10 mM CaCl$_2$ |
| | 10 mM Tris-HCl (pH 7.4) |
| | filter sterilize |
| Solution A | 0.2M Tris-HCl (pH 7.5) |
| | 0.1M MgCl$_2$ |
| | 0.5M NaCl |
| | 0.01M dithiothreitol (DTT) |
| Solution B | 0.2M Tris-HCl (pH 7.5) |
| | 0.1M MgCl$_2$ |
| | 0.1M DTT |
| 20X SSPE | 4.4 g NaOH |
| | 7.4 g Na$_2$EDTA |
| | 27.6 g NaH$_2$PO$_4$.H$_2$O |
| | 210 g NaCl |
| | pH adjusted to 7.5–8.0 with NaOH |
| | H$_2$O to 1 liter |
| 10X Transfer Buffer | 5.0 g NaCl |
| | 96.8 g Trizma Base |
| | 9.74 g glycine |
| | water to 1 liter |

Example I

Construction of Vector pTB04

Plasmid AM6 is a derivative of the HBV genome shown in FIG. 6, wherein the pBR322 plasmid is inserted at the BamHI site at position 26.

The vector pTB04 contains the gene encoding the 281 amino acid preS$_2$ form of the hepatitis B surface antigen. The gene was constructed in three segments: the C-terminal 75% of the structural gene, an N-terminal linker encoding 13 amino acids, and the remaining central portion. The plasmid AM6 containing the preS$_2$ gene, adw seratype, was the source of the C-terminal portion and the middle portion of the preS$_2$ gene used here. The sequence is disclosed in Valenzuela et al., ICN-UCLA *Symposia on Animal Virus Genetics*, p. 57–70 (1980), with the following modification:

| | |
|---|---|
| native sequence | ATG—CAG—TGG—AAT—TCC |
| mutagenized sequence | ATG—CAG—TGG—AA<u>C</u>—TCC |

A. C-terminal portion of preS$_2$ (All restriction enzymes were obtained from Boehringer Mannheim, and used according to manufacturer's instructions).

The C-terminal portion was isolated from the plasmid AM6 (FIG. 1) by digestion with DraI, which cuts the HBV genome at two places, one of which is at the codon for the last amino acid of the surface antigen. The ends were dephosphorylated by treatment with calf intestinal alkaline phosphatase in a 30 µl reaction volume (1U enzyme at 37° C. for 1 hour in 50 mM Tris.Cl, pH 9.0, 1 mM MgCl$_2$, 100 µM ZnCl$_2$, 1 mM spermidine). The entire digest was phenol extracted and ethanol precipitated (Maniatis et al.). An octameric StuI linker (AAGGCCTT) was synthesized by a DNA synthesizer from Applied Biosystem Model 380A using cyanoethylphosphoramidite chemistry. 1 µg of StuI linkers was dissolved in distilled water. A 10 ng aliquot was removed and labeled with phosphate in a 50 µl total volume containing 70 nM Tris.Cl, pH 7.6, 10 nM MgCl$_2$, 5 µM dithiothreitol, 1 nM ATP and 10 units of polynucleotide kinase for 30 minutes at 37° C. The linkers were heated to 90° C. to terminate the enzymatic reaction, and slow-cooled to room temperature to facilitate double stranded DNA formation. The StuI linkers were added to the DraI digest above and ligated with T4 ligase as follows. The reaction occurred in a 10 µl volume containing 6.6M Tris.Cl, pH 7.6, 5 mM MgCl$_2$, dithiothrietol, 1 mM ATP and 1 Weiss unit of T4 ligase for 1 hour at 23° C. The ligation reaction was terminated by phenol extraction followed by ethanol precipitation. A StuI restriction digest was then performed with >50 U of enzyme overnight to remove multimers of the StuI linker. The combination of DraI digestion and StuI linkers restored the translation stop codon removed by DraI digestion.

The StuI-linkered DraI fragments were digested with XbaI, which yielded the desired StuI/XbaI fragment of approximately 600 bp; it was isolated from a 0.8% preparative agarose gel. This fragment contained the C-terminal 75% of the gene and was cloned into the vector pYM4 (FIG. 2) which had been digested with XbaI and StuI, and dephosphorylated as above. (pYM4 can be obtained from plasmid pYM30 by digesting pYM30 with ClaI and re-ligating the ends. pYM30 is available in an *E. coli* host deposited at the Northern Regional Research Center, United States Department of Agriculture, Peoria, Ill., accession number NRRL B-15890). The 5.7 Kb restriction fragment of pYM4 was isolated from a 0.8% preparative agarose gel. Vector pYM4 was employed solely for its convenient restriction sites. 50 ng of the vector and 500 ng of the insert were ligated at 23° C. for 1 hour in 50 mM Tris HCl pH 7.4, 10 mM HgCl$_2$, 10 mM dithiothreitol, 1 nM spermidine, 1 mM ATP with 1 Weiss Unit of T4 ligase in a 10 µl volume. The ligation reaction was used directly to transform competent MC1061 cells (*E. coli*) to ampicillin resistance. *E. coli* strain MC1061 is available at the Northern Regional Research Center, United States Department of Agriculture, Peoria, Ill., accession number NRRL-18016. MC1061 has the following genotype: F(−), ara D139 delta (lacIPOZY) X74 galk galU hsr hsm(+) rpsL delta (araABOIC leu) 7697. MC1061 was rendered for transformation in the following manner. A mid-log culture (50 ml) of *E. coli* MC1061 was harvested by centrifugation in a Damon IEC DPR600 at 3,000 rpm for 5 min. at 4° C. and washed in 10 nM NaCl. The culture was resuspended in 25 ml of 50 mM CaCl$_2$ for 30 minutes at 0° C. The cells were centrifuged as above and resuspended in 2 ml of 50 mM CaCl$_2$. For transformation, the ligation reaction was added to 100 µl of the competent cell suspension and incubated at 0° C. on ice for 15 minutes, heat shocked at 37° C. for 5 minutes and incubated at 23° C. for 5 minutes. The cells were plated directly onto LB agar plates containing 50 µg/ml ampicillin. The plates were incubated at 37° C. for 10–16 hours. The resulting colonies were harvested and characterized by restriction digestion. Cells were grown in 5 ml of L-broth containing 50 µg/ml ampicillin for 5 hr. at 37° C. and DNA was prepared by the method of Birnboim and Doly [*Nucleic Acids Research* 7:1513 (1979)].

The minipreps were digested with BamHI and XbaI. Cultures yielding a 1.5 Kb Xba/Bam fragmented were deemed to have the insert and a large scale DNA prep of one culture was purified as above, followed by banding on a cesium chloride-ethidium bromide gradient. This clone was called pHS1.

The plasmid pHS1 was digested with StuI, dephosphorylated as above, phenol extracted and ethanol precipitated. EcoRI linkers (GGAATTCC) synthesized as above were phosphorylated, self annealed, and ligated to this blunt ended DNA. Excess linkers were removed by overnight EcoRI digestion and the DNA was subsequently digested with XbaI following phenol extraction and ethanol precipitation. A doublet containing the 600 bp XbaI-EcoRI fragment of interest and a vector fragment of 582 bp (XbaI-EcoRI) was isolated by 1.0% preparative gel electrophoresis. These fragments (500 ng) were ligated into XbaI-EcoRI-digested and dephosphorylated pUC18 (50 ng) as described above and used to transform MC1061 to ampicillin resistance as described above. Restriction digests of miniprep DNA were used to determine which of the two fragments had been cloned. The undesirable fragment had a ClaI site such that a ClaI/XbaI double digest would yield fragments of approximately 560 bp+2400 bp, whereas the correct fragment yielded a linear 3 Kb fragment upon ClaI/Xb digestion. Candidates were digested with EcoRI and XbaI to yield fragments 600 bp+2400 bp. One such clone was purified on large scale and termed pHS2-B. This contains an EcoRI site after the last codon at the C-terminal region of the complete preS$_2$ gene.

B. Middle Portion of preS$_2$ Gene

The middle portion of the preS$_2$ gene was cloned as follows. The plasmid AM6 was digested with XbaI and BamHI and a fragment of 250 bp was isolated from a 0.8% preparative agarose gel. This fragment (50 ng) was ligated as described above to 50 ng of pUC18 digested with XbaI and BamHI and dephosphorylated. The ligation reaction was used to transform *E. coli* strain MC1061 to ampicillin resistance as above. Minipreps were digested with BamHI and those containing a 2.7 Kb linear fragment were chosen. One isolate was grown on large scale and DNA was isolated and purified as described. This clone is called pPS1. The clone was cut with EcoRI and BamHI and the vector band isolated and purified by 0.8% preparative agarose gel electrophoresis. To this vector was ligated the following kinased double stranded oligonucleotide synthesized as above:

```
        EcoRI      PstI    BamHI
5' AATTCAATCCGTCTGCAG 3'
    3' GTTAGGCAGACGTCCTAG 5'
```

The ligation reaction was used to transform *E. coli* MC1061 to ampicillin resistance. Minipreps were characterized by PstI digestion. One clone containing a 250 bp PstI fragment was chosen, a large scale DNA prep was performed, and the plasmid pPS2 was isolated.

C. N-terminal Portion of preS$_2$ Gene

The N-terminal region encompassing the EcoRI linker and the coding sequences for the first thirteen amino acids was generated from a synthetic oligonucleotide containing the following sequence synthesized as above:

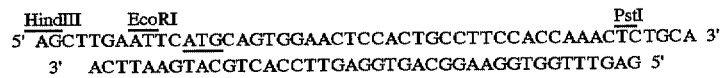

```
     HindIII    EcoRI                                PstI
5' AGCTTGAATTCATGCAGTGGAACTCCACTGCCTTCCACCAAACTCTGCA 3'
    3'   ACTTAAGTACGTCACCTTGAGGTGACGGAAGGTGGTTTGAG 5'
```

This fragment contained HindIII and PstI ends as well as an EcoRI sequence preceding the ATG. This sequence was cloned into HindIII- and PstI-digested and dephosphorylated pUC18 by ligating a ten-fold excess of the oligo into the vector and characterizing the transformants by the presence of a small EcoRI site (~75 bp). Such a clone was designated pTBO-2A.

The middle portion of the gene was added by digesting the vector pTBO-2A with PstI and XbaI; the insert was the 250 bp Pst-Xba fragment from pPS2. Transformants were characterized by the presence of a >300 bp EcoRI fragment as well as 290 bp XbaI/HindIII fragment. The correct isolate was termed pTB0-3. The complete preS$_2$ gene was achieved by inserting the HindIII/XbaI fragment from pTB0-3 into XbaI/HindIII-digested pHS2B. Ampicillin resistant transformants were characterized as above by the presence of a 825 bp EcoRI fragment. This construct was termed pTB04.

Example II

Construction of Vector pTB05A

A vector containing the gene coding for preS$_2$ was constructed from vectors pA0804 and pTB04 (Examples V and I, respectively). 2 µg of pA0804 was digested with EcoRI as before and treated with alkaline phosphatase in a 30 µl reaction volume (1 U enzyme at 37° C. for 1 hour in 50 mM Tris.Cl pH 9.0, 1 mM MgCl$_2$, ZnCl$_2$, 1 mM spermidine). pTB04 was subjected to EcoRI digestion and an 825 bp fragment encoding the preS$_2$ gene was released. This fragment was purified using preparative agarose gel electrophoresis using 0.8% agarose. 500 ng of the fragment and 50 ng of pA0804 were ligated using methods described in Example I. The resulting vector was used to transform MC1061 to ampicillin resistance using the method described in Example I. The DNA was isolated using the method of Birnboim and Doly [*Nucleic Acids Research* 7:1513 (1979)] and characterized by digestion with PstI. A clone containing a 2.1 Kb PstI fragment was determined to have the insert in the correct orientation and was designated pTB05A.

Example III

Construction of pTB047 Template

1 µg of double stranded m13mp18 DNA (from Example I) was digested with EcoRI and dephosphorylated by treatment with calf intestinal alkaline phosphatase in a 30 µl reaction volume (1 U enzyme at 37° C. for 1 hour in 50 mM Tris.Cl, pH 9.0, 1 mM MgCl$_2$, 100 mM ZnCl$_2$, 1 mM spermidine). The 825 bp EcoRI fragment containing the preS$_2$ gene was isolated from pTB04 (see Example I) by digestion with EcoR1, and was then isolated from a 0.8% preparative agarose gel. 50 ng of m13mp18 vector and 500 ng of the EcoRI insert were ligated with T4 DNA ligase as follows. The reaction occurred in a 10 µl volume containing 6.6M Tris.Cl, pH 7.6, 5 mM MgCl$_2$, 5 mM dithiothrietol, 1 mM ATP and 1 Weiss unit of T4 ligase for 1 hour at 23° C.

The ligation mixture was then used to transform *E. coli* JM103 cells which had been made competent in the following manner. A mid-log culture (50 ml) of *E. coli* JM103 cells was harvested by centrifugation in a Damon IEC DPR600 clinical centrifuge at 3,000 rpm for 5 min. at 4° C. and washed in 10 mM NaCl. The culture was resuspended in 25 ml of 50 mM CaCl$_2$ for 30 min. at 0° C. The cells were centrifuged as above and resuspended in 2 ml of 50 mM CaCl$_2$.

For transformation, the ligation reaction was added to 100 µl of the competent cell suspension and incubated at 0° C. on ice for 15 minutes, heat shocked at 37° C. for 5 minutes, and incubated at 23° C. for 5 minutes. The cells were then plated in soft agar containing IPTG and X-gal and spread on to LB media, and incubated at 37° C. overnight, and the plates were screened for clear plaques.

In order to determine which plaques had the insert in the correct orientation, double-stranded DNA was prepared and separate digests with EcoRI and XbaI were performed. One was found to have the initiator methionine of the insert close to the M13 universal primer, and would then generate a template containing the anti-sense strand of the insert. This was designated pTB047.

Example IV

Construction of pTBO-6 and pHB6

A DNA sequence encoding a 226 amino acid form of HBsAg (the S form) was created by deleting the 165 bp encoding the first 55 amino acids of preS$_2$. This was accomplished by subjecting the template pTB047 (from Example III) to M13 primer-directed deletion mutagenesis using the following oligonucleotide primer:

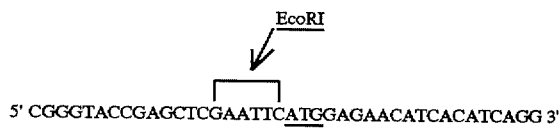

This was synthesized using an Applied Biosystems DNA Synthesizer Model 380A using cyanoethylphosphoramidite chemistry. Mutagenesis was performed according to the following.

A large scale miniprep was performed on positive plaques which had been incubated for approximately 7 hours in 2 mls of LB media. 25 mls of LB media was inoculated with 250 µl of freshly grown JM103 cells. The culture was grown for 1 hour and inoculated with 100 µl of the 7 hour old plaque culture. The culture was then grown overnight. The culture was centrifuged twice at 10,000 rpms for 10 minutes on a Sorvall RC-5B rotor SS34 to clear the supernatant. 3.5 ml of 20% PEG/2.5M NaCl was added to the culture and it was incubated for 5 hours at 4° C. The culture was then centrifuged as above for 10 minutes. The supernatant was discarded and the pellet was resuspended in 2 mls of TE buffer. The pellet was then extracted with phenol (equilibrated with TE), extracted once with phenol/chloroform, extracted twice with CHCl$_3$ and once with ether. 8M LiCl was added to attain a final concentration of 0.8M. 3 volumes of ethanol were added and the solution left overnight at 20° C. to precipitate the DNA present. The solution was next centrifuged for 10,000 rpms for 10 minutes as previously described and rinsed with 70% ethanol. The precipitate was resuspended in 150 µl of 10 mM Tris.Cl, pH 7.4.

One pmole of M13 recombinant template was mixed with 20 pmole of the oligonucleotide primer, and 1 µl of solution A. dH$_2$O was added to give a final volume of 10 µl. The sample was incubated at 65° C. for 5 minutes, and the temperature was then reduced to 37° C. for 30 minutes.

The following was then added to the sample:

| | |
|---|---|
| Solution B | 1 µl |
| 10 mM dATP | 1 µl |
| 10 mM dCTP | 1 µl |
| 10 mM dGTP | 1 µl |
| 10 mM dTTP | 1 µl |
| 5 u/µl Klenow | 2 µl |
| dH$_2$O | 3 µl |
| | 20 µl | and allowed to incubate at 15° C. for at least 4–6 hours.

The sample was then diluted 1:40 with dH$_2$O. 5 µl was used to transform 6 tubes of competent JM103 cells (200 µl each). The transformed JM103 cells were plated on LB media in a soft agar overly. The positive plaques were then screened by filter hybridization. A hybridization probe complementary to the oligonucleotide primer was synthesized as described above. 15 pmole of this probe was incubated at 65° C. for 10 minutes in a total volume of 25 µl. 3 µl of 10× kinase buffer (Maniatis et al.), 1 µl 10 mM ATP, and 1 µl polynucleotide kinase (100 U/µl) were added. The sample was incubated for 1 hour at 37° C. and run over a G50 Sephadex column. The first peak off the column was collected.

Nitrocellulose filters were prepared for hybridization with the above probe by placing and orienting the filters on the transformation plates for 5–10 minutes. The filters were then removed from the plates and floated on a denaturing solution (1.5M NaCl, 0.5N NaOH) for 3 minutes with the backside on top of the solution. The filters were submerged in the denaturing solution for 5 minutes, and then transferred to a neutralizing solution (1M Tris.Cl, pH 8, 1.5M NaCl) for 5 minutes. The neutralized filter was then transferred to 2×SSC (1×SSC is 150 mM NaCl, 15mM NaCitrate) for 5 minutes. The filter was air dried and baked for 1 hour at 80° C. under a vacuum. The filters were prehybridized for 1 hour at 65° C. in a sealed plastic bag containing 5 ml of hybridization buffer, 10× Denhardts (1× Denhardts is 0.02% Ficoll, 0.02% polyvinyl pyrrolidone, 0.02% bovine serum albumin) 0.5% SDS, and 5×SSPE. The buffer was replaced with 5 ml/filter of fresh hybridization buffer. The radioactive complementary oligonucleotide previously prepared was first incubated at 65° C. for 5 minutes, and then enough probe was added to the fresh hybridization buffer containing the filter to give 1×10$^6$ cpm/ml. Hybridization was performed at 5° C. below the calculated melting temperature of the probe for 4 hours.

The filters were then washed three times for 10 minutes each with 6×SSC at room temperature. The filters were finally washed one time with 6×SSC at the hybridization temperature. The filters were placed on a 3 MM Whatman paper to dry, and then exposed to film (marked for orientation) overnight. Three positive plaques were each picked and grown separately in 2 mls of LB broth at 37° C. for 5 hours.

Mini template preps were performed on each of these positive plaques. One ml of the plaque culture was transferred into an Eppendorf tube and centrifuged for 5 minutes in an Eppendorf Model 5414 Centrifuge. 800 µl of the supernatant was recovered and 200 µl of 200% PEG 2.5M NaCl added thereto. The supernatant was then incubated at room temperature for 10 minutes, and centrifuged for 10 minutes in the Eppendorf centrifuge. The supernatant was removed by aspiration and the pellet was redissolved in 200 µl TE (10 ml Tris, pH 7.4; 1 mM ETDA). The redissolved pellet was then phenol/chloroform extracted and the template DNA in the upper aqueous phase was precipitated by the addition of a LiCl solution unitl a 0.8M concentration of LiCl was reached. 2½–3 volumes of ethanol was added and the sample was precipitated on dry ice for 5 minutes. The precipitate was centrifuged for 10 minutes as described above. The final volume was brought up to 150 µl TE.

200 µl of competent JM103 cells were transformed with the recovered DNA. 1 µl of a 1/10 dilution of the isolated phage DNA was used in the transformation. The transformation mixture was plated and plaques were screened with oligonucleotides as previously described.

A large scale miniprep was performed on positive plaques which had been incubated for approximately 7 hours in 2 mls of LB media. 25 mls of LB media was inoculated with 250 µl of freshly grown JM103 cells. The culture was grown for 1 hour and inoculated with 100 µl of the 7 hour old plaque culture. The culture was then grown overnight, and then centrifuged twice at 10,000 rpms for 10 minutes on a Sorvall RC-5B with a SS34 rotor to clear the supernatant. 3.5 ml of 20% PEG/2.5M NaCl was added to the culture and it was incubated for 5 hours at 4° C. The culture was then centrifuged again as above for 10 minutes. The supernatant was discarded and the pellet was resuspended in 2 mls of TE buffer. The pellet was then extracted with phenol, equilibrated with TE, extracted with phenol/chloroform once, extracted twice with $CHCl_3$ and once with ether. 8M LiCl was added to attain a final concentration of 0.8M. 3 volumes of ethanol were added and the solution left overnight to precipitate the DNA present. The solution was centrifuged for 10 minutes at 10,000 rpm as previously described and rinsed with 70% ethanol. The precipitate was resuspended in 150 µl of 10 mM Tris (pH 7.4).

Positive colonies were identified by colony hybridization [Grunstein and Hogness, *PNAS* 72,3961 (1975)] and sequenced using dideoxy sequencing to find the M13 constructs with the correct mutation. RF DNA was recovered using the alkaline lysis method of Maniatis et al. A 678 bp EcoRI fragment was isolated on a 0.8% preparative agarose gel and subcloned into pA0804 and pA0811 (see Example V and VI, respectively). *E. coli* MC1061 cells were transformed with either of these two vectors as described in Example I. Transformants containing the proper orientation were identified by XbaI digestion of DNA minipreps (also as described in Example I). One transformant derived from pA0804 was called pTB06; a pA0811 derived transformant was called pHB6.

Example V

Construction of pA0803 and pA0804 pA0804 is a vector capable of site-specific disruption of the *P. pastoris* AOX1 locus. It contains the following elements: the AOX1 promoter and transcription terminator separated by a unique EcoR1 cloning site; the wild-type Pichia HIS4 gene; a genomic segment of DNA from the 3' end of the AOX1 locus downstream of the transcription terminator; sequences necessary for selection and replication in a bacterial host. The components are arranged such that a restriction digest of the vector releases a DNA fragment containing the expression cassette and selective marker whose ends are homologous to a continuous portion of the genome, the AOX1 locus, and can be stably inserted into the chromosome during transformation.

pA0804 is a derivative of the hepatitis B surface antigen expression plasmid pBSAGI5I (NRRL 18021). It was assembled in a pBR322-based plasmid containing the following modifications. pBR322 was digested with EcoR1, followed by phenol extraction and ethanol precipitation. The ends were then filled in using Klenow polymerase. 2 µg of EcoR1 digested pBR322 was incubated at room temperature for 15 minutes in a 25 µl reaction volume containing 50 mM Tris.Cl, pH 7.2, 10 mM $MgSO_4$, 100 µM dithiothrietol, 50 µg/ml bovine serum albumin, 100M dATP, 100 µM dTTP, and 1 unit of Klenow polymerase. Following phenol extraction and ethanol precipitation, the DNA was ligated to reclose the plasmid and the ligation reaction was used to transform *E. coli* MC1061. Transformants were screened for the absence of the EcoRI site as well as the presence of diagnostic sites such as PstI, PvuII and SalI. Such a plasmid was called pBR322-RI.

This plasmid was further modified to incorporate a BglII site at the PvuII site. The plasmid was digested with PvuII and phosphorylated BglII linkers (GAGATCTC) were added in a blunt end ligation. The excess linkers were removed by overnight BglII digestion and the plasmid was reclosed using T4 DNA ligase. The ligation reaction was used to transform *E. coli* MC1061 to ampicillin resistance. Transformants were characterized by restriction digestion with BglII to indicate the presence of a BglII site and with a SalI/BglII digest indicating that the BglII site was at the former PvuII site. This plasmid was designated pBR322 BglII-RI.

pA0804 and pA0811 were created by scavenging DNA fragments from pBSAGI5I and assembling them in pBR322 BglII-RI. The 3' targeting segment of the AOX1 locus was removed from pBSAGI5I as a 700 bp BglII/XhoI fragment, of which 50 ng were ligated to 5 ng of the parent plasmid which had been digested with SalI and BglII. The ligation reaction was used to transform *E. coli* MC1061 to ampicillin resistance. Transformants were characterized by a BamHI/BglII digest of mini prep DNA as described in Example 1, such that an approximately 900 bp fragment was observed. One such transformant was chosen and DNA was purified on large scale. Such a plasmid was named pA0801.

The plasmid pBSAGI5I was digested with ClaI and a 2.1 Kb fragment containing the promoter-gene-terminator expression cassette was isolated. The 2 µg of pA0801 was digested with ClaI and treated with alkaline phosphatase in a 30 µl reaction volume (1 U enzyme at 37° C. for 1 hour in 50 mM Tris HCl pH 9.0, 1 mM $MgCl_2$, 100 µM $ZnCl_2$, 1 mM spermidine). 50 ng of the ClaI fragment was ligated to 5 ng of the pA0801 vector and the ligation reaction was used to transform *E. coli* MC1061 to ampicillin resistance. These colonies were characterized by BglII digestion to ascertain that the fragment was inserted and was in the correct orientation yielding a spectra of 2.3 and 2.7 Kb fragments. This single transformant was called pA0802.

The plasmid pA0802 was digested at the unique StuI site at the 3' end of the hepatitis B surface antigen gene. EcoRI linkers were phosphorylated, annealed, and ligated to the StuI digested plasmid. Excess linkers were removed by overnight EcoRI digestion. The EcoRI digestion also cuts at the 5' end of the HBsAg structural gene, hence removing the gene. Upon religation, the promoter and transcription terminator were joined by a unique EcoRI cloning site. Ampicillin resistant transformants were characterized again by BglII digestion and a transformant with the correct spectrum (2.3 & 2.1 Kb) was identified and called pA0803.

The plasmid pA0803 was digested with BamHI and the 2.7 Kb BglII fragment from pYM10 (FIG. 8) was isolated by preparative agarose gel electrophoresis and ligated to the BamHI-digested dephosphorylated pA0803. [pYM10 is a derivative of pYJ30 (NRRL B-15890) with the BamHI site at 2959 destroyed]. Transformants were characterized by the presence of an XbaI site yielding a fragment of 7.4 Kb and a BglII spectrum of 2.3 and 5.1 Kb. This plasmid was called pA0804.

Example VI

Construction of pA0811

A second related plasmid containing the Saccharomyces ARG4 gene instead of the Pichia HIS4 gene was also constructed. One possible source of the ARG4 gene is the 2.0 Kb HpaI fragment obtained from pYM25, a plasmid in an *E. coli* host, NRRL B-18015. This strain is available from the Northern Regional Research Center of the United States Department of Agriculture, Peoria, Ill.

The fragment was purified from a 0.8% preparative agarose gel. 500 ng of the fragment was ligated to 50 ng of BamHI digested, filled in pA0803 (see Example V). The ligation reaction was used to transform *E. coli* MC1061 to ampicillin resistance. Transformants were characterized by BglII digestion, and the correct insert size was verified by agarose gel electrophoresis. This plasmid was called pA0811.

Example VII

Yeast DNA Miniprep $10^4$ cells/ml were grown in 5 ml YPD at 30° C. overnight and then pelleted using a Damon IEC DPR600 clinical centrifuge at 3,000 rpm for 5 minutes. The pellet was resuspended in 0.5 ml of 1M sorbitol, 0.1 ml 0.5M EDTA, pH 7.5 and the sample transferred to a 1.5 ml microfuge tube. 0.02 ml of 2.5 mg/ml Zymolyase 60,000 (Miles Laboratories) was added, and the sample was incubated at 37° C. for 60 minutes. The cells were pelleted using the microfuge for 1 minute at high speed, and resuspended in 0.5 ml of 50 mM Tris.Cl, pH 7.4 and 20 mM EDTA. 0.05 ml of 10 % SDS was added, the sample mixed, and incubated at 65° C. for 30 minutes. 0.2 ml of 5M potassium acetate was added and the sample was incubated on ice for 60 minutes. The sample was again spun in a microfuge at high speed for 5 minutes.

The supernatant was transferred to a fresh 1.5 ml microfuge tube and 1 volume of isopropanol at room temperature was added. The sample was mixed and allowed to sit at room temperature for 5 minutes, then spun very briefly (10 seconds) in a microfuge at high speed. The supernatant was poured off and the pellet air dried. After resuspending the pellet in 0.3 ml of 10 mM Tris.Cl, pH 7.4 and 1 mM EDTA, 15 µl of a 1 mg/ml solution of pancreatic RNase was added, and the sample was incubated at 37° C. for 30 minutes. 0.03 ml of 3M sodium acetate was added, the sample mixed, and 0.2 ml of isopropanol added. The sample was spun in a microfuge at high speed to pellet the DNA. The supernatant was then poured off, the pellet dried and resuspended in 0.1–0.3 ml of 10 mM Tris.Cl, pH 7.4 and 1 mM EDTA. (Note: Before using the DNA in a restriction digest, it may be necessary to spin the solution for 15 minutes at high speed in the microfuge to remove any insoluble material which may inhibit the digestion).

Example VIII

Development of Mixed Particle Strains

Two mixed particle strains containing expression cassettes encoding the S (p24) and preS$_2$ (p31) forms of the Hepatitis B surface antigen were constructed as follows. *Pichia pastoris* PPF1 (arg4 his4) was transformed with 1 µg of uncut pHB6 using the spheroplast transformation technique described by Cregg et al., *Bio/Technology* 5,479 (1987). (pHB6 is a subclone of pA0811 containing the S gene described in Example IV and VI). Transformants demonstrating arginine prototrophy were regenerated on minimal media containing histidine and screened for the site of integration as follows.

DNA from these transformants and from wild type *Pichia pastoris* was prepared as described in Example VII, digested with EcoR1 and subjected to electrophoresis on 0.8% agarose. Southern blots of these DNAs were performed (*Maniatis* et al. 1983) and the filters hybridized with an AOX1 specific probe (pPG4.0 NRRL#15868) or with a HIS4 specific probe (pYM4). pYM4 is described in Example I. The site of integration was determined by comparing the spectrum of hybridization of a given transformant with the wild type strain. Any alteration in the size of the wild type band was evidence of integration at that locus. The transformant containing an integration at the 5'-end of the AOX1 locus, and still containing a wild type AOX1 gene as well as a HIS4 mutation, was called PPF1/pHB6.

This strain was then transformed with BglII-cut pTB05A (from Example II) as described above. Transformants demonstrating histidine prototrophy were regenerated on minimal media and screened for the "methanol slow" (Mut-) phenotype, which indicated integration of the AOX1 locus. Screening for the phenotype was performed in the following manner.

Transformants were pooled by scraping the surface of the plate in the presence of sterile distilled water and sonicated at low output for 15 seconds. They were subsequently diluted to an $A_{600}$ 0.1 and plated at dilutions of $10^{-3}$ and $10^{-4}$ in duplicate onto minimal plates containing glycerol as the carbon source, and incubated at 30° C. for 2–3 days. They were then replica-plated onto minimal plates to which 100 µl of methanol was added in the vapor phase. After a 24-hour incubation at 30° C., it was apparent that 10–20% of the transformants were growing more slowly on methanol than the rest of the transformants. Ten of these slow growing colonies were then selected for further analysis. They were picked from the minimal plate containing glycerol, grown in shake flasks as described in Example IX, and assayed for 22 nm—like particle activity as described in Example XI. The transformants were characterized as described above for pHB6. One resulting strain was called PPF1/pTB012-1, and expressed one copy of both the p24 and p31 proteins.

Another strain was identified which had integrated two copies of the preS$_2$ expression cassette. It was called PPF1/pTB012-2 and it expressed two copies of the preS$_2$ gene and one copy of the S gene.

Particle expression levels are shown in Table 3.

TABLE 3

| Strain | Cassette | Proteins | Particle Expression Levels (AUSRIA ™) |
|---|---|---|---|
| PPF1/pTB012-1 | 1 preS$_2$ | p31 | ~150–200 |
|  | 1 S | p24 | µg particle/ml lysate |
| PPF1/pTB012-2 | 2 preS$_2$ | p31 | ~150–200 |
|  | 1 S | p24 | µg particle/ml lysate |

In addition, SDS/PAGE analysis and silver staining of a partially purified protein preparation indicated the presence of both p24 and p31.

Example IX

Shake Flask Expression Studies

Prior to fermentation, all strains were grown in shake flasks as follows to ascertain expression levels. Routinely, a transformant was seeded into 0.67% yeast nitrogen base containing 2–5% glycerol and grown overnight at 30° C. into middle to late log phase. The cells were then collected by centrifugation rising a Damon IEC DPR600 clinical centrifuge at 3,000 rpm for 5 minutes. The pellet was washed in sterile water twice, then seeded at a density of 0.5 $A_{600}$ units/ml into phosphate buffered 0.67% YNB containing 1% methanol and grown for 4–6 days at 30° C. with moderate shaking. At various times, aliquots of 50 $A_{600}$ units were removed and stored at −20° C. Protein extracts were prepared from these aliquots to be used for an AUSRIA™ (see Example XI) and Western blot analysis [Towbin et al. PNAS 76, 4350 (1979)]. Antibody was Lot #702106 from Calbiochem, used at a 1:1000 dilution. Aliquots of cells (100 A600 units) were transferred to 13×100 mm borosilicate culture tubes and washed twice by centrifugation in a Sorvall Model RC-5B at 12,000 rpm, 4° C. with 20 volumes of lysing buffer [0.5M $NaCl_{1, 0.1}$% Triton X-100 ("/v), 1M phenylmethylsulfonyl fluoride and 10 mM sodium phosphate, pH 7.5)]. Cell samples were resuspended with 0.5 grams of acid-washed glass beads (0.5 mm) plus 0.35 ml of lysing buffer, and agitated for eight, one-minute intervals at maximum speed using a vortex mixer. Between intervals, the mixture was cooled on ice for at least one minute. After lysing was completed, the solution of broken cells was removed and the glass beads were washed with 0.35 ml of lysing buffer. The two solutions were then combined and centrifuged using the Sorvall RC-5B at 13,000 rpm, 4° C., to remove cellular debris. Protein samples were then assayed by AUSRIA™ and by Western blot analysis. Protein concentration was determined by the Lowry method after TCA precipitation.

Example X

Fermentation Expression Studies

Fermentations were performed as follows. Five hundred ml of Yeast Nitrogen Base (YNB) +2% glycerol in a Fernbach Flask was inoculated from a seed culture or a minimal glucose plate of the culture. (Plates may be maintained by monthly passage with no detectable strain deterioration). After one day of shaking at 200 rpm and 30° C., the inoculum was seeded into 7.5-liter minimal medium (Table 4) containing 480 g glycerol, 40 mg biotin, and 40 ml trace salts solution (Table 5). The fermentor was maintained at 30° C. and pH 5.5 while the culture grew in batch mode until the glycerol was exhausted (about 24 hours). The pH was controlled by the addition of $NH_3$ gas. Glycerol exhaustion was noted by a sharp decline in the $CO_2$ evolution and a sharp rise in the dissolved oxygen (or decrease in oxygen uptake rate). A methanol feed was initiated at 18 ml/hr to bring the fermentor level up to ~0.5% MeOH, and maintained at this level. The flow rate was adjusted based on the actual methanol consumption rate. Twenty ml aliquots of trace salts were added at approximately two day intervals to maintain the methanol consumption rate. The level of HBsAg increased for approximately 7–8 days on the methanol feed.

TABLE 4

| Medium Composition (7.5-Liter) | |
|---|---|
| 480 g | glycerol |
| 40 mg | biotin |
| 134 ml | $H_3PO_4$ (85%) |
| 5.8 g | $CaSO_4.2H_2O$ |
| 92 g | $H_2SO_4$ |
| 75 g | $MgSO_4.7H_2O$ |
| 21 g | KOH |

TABLE 5

| $IM_1$ Trace Salts Solution | |
|---|---|
| Cupric Sulfate.$5H_2O$ | 0.06 |
| Potassium Iodide | 0.08 |
| Manganese Sulfate.$H_2O$ | 0.30 |
| Sodium Molybdate | 0.20 |
| Boric Acid | 0.02 |
| Zinc Sulfate.$H_2O$ | 2.00 |
| Ferric Chloride.$H_2O$ | 4.8 |
| Sulfuric Acid | 5.00 ml/liter |

Example XI

AUSTRIA™ RIA Protocol

The Abbott AUSRIA™ assay kit was used to measure the amount of HBsAg synthesized by the Pichia production system. The antibody contained in the kit binds to HBsAg particles, not HBsAg monomers. All dilutions were made in 1.0% BSA, 0.02% Na Azide in phosphate buffered saline, pH 7.4. The procedure followed was essentially as outlined in the kit instructions. The standard curve was prepared as follows.

| Tube # | ng. in assay | Buffer (µl) | Positive Control (µl) |
|---|---|---|---|
| 1–4 | None NSB | none | 200 buffer only |
| 5–6 | 0.1 | 195 | 5 |
| 7–8 | 0.2 | 190 | 10 |
| 9–10 | 0.5 | 175 | 25 |
| 11–12 | 1.0 | 150 | 50 |
| 13–14 | 2.0 | 100 | 100 |
| 15–16 | 3.0 | 50 | 150 |
| 17–18 | 4.0 | none | 200 |

The wells of the microtiter dish were labeled as follows.

| | AA | BB | CC | DD |
|---|---|---|---|---|
| 1 | 1 | 2 | 3 | 4 |
| 2 | 5 | 6 | 7 | 8 |
| 3 | 9 | 10 | 11 | 12 |
| 4 | 13 | 14 | 15 | 16 |
| 5 | 17 | 18 | 19 | 20 and so on . . . |

The beads were first added to each well, followed by the buffer, and finally the standard (positive control) or the diluted sample. Unknowns were diluted to obtain signals within the range of the standard curve. Estimates of sample concentrations in mg/ml were typically divided by 0.02 to obtain the dilution to be used. Usually 100 µl of the sample was added to the well containing 100 µl of buffer. The wells were covered and the tray gently tapped against the bench top. The samples were then incubated overnight at room temperature to attain maximum binding efficiency. The next morning each well was washed 4 times with deionized water using the Pentawash system provided by Abbott Labs. 200 μl of the $^{125}$I anti-HBs were added to each well, the tray was gently tapped, and then incubated in a 45° C. water bath for 1 hr. The beads were washed as before and counted. Concentrations of unknowns were determined from the standard curve.

That which is claimed is:

1. Antigenic Hepatitis B virus (HBV) particles comprising HBV S and preS2 proteins made by a process which comprises:

(a) transforming a *Pichia pastoris* strain with a first expression cassette comprising a structural gene for a hepatitis B virus S protein operably linked to a 5' regulatory region and a 3' termination sequence obtainable from *Pichia pastoris*; and (b) transforming said *Pichia pastoris* strain with a second expression cassette comprising a structural gene for the hepatitis B virus preS$_2$ protein operably linked to a 5' regulatory region and a 3' termination sequence obtainable from *Pichia pastoris*; and (c) culturing the resulting transformed *Pichia pastoris* strain under suitable conditions to obtain the production of said HBV particles.

2. Recombinantly produced HBV particles consisting of S and preS$_2$ proteins.

3. Hepatitis B virus (HBV) particles comprising S and preS$_2$ proteins produced in a methylotrophic yeast.

* * * * *

UNITED STATES PATENT AND TRADEMARK OFFICE
CERTIFICATE OF CORRECTION

PATENT NO. : 5,670,630
DATED : September 23, 1997
INVENTOR(S) : Gregory P. Thill It is certified that error appears in the above-identified patent and that said Letters Patent are hereby corrected as shown below:

Column 1, line 52: "PreS2" should read --$PreS_2$--

Column 2, line 7: "infections" should read --infectious--

Column 2, line 15: "bas" should read --has--

Column 2, line 35: "theproduction" should read --the production--

Column 4, line 48: "5 kb" should read --5.7 kb--

Column 4, line 49: after "isolated" insert --by--

Column 8, line 18: "a" should read --and--

Column 8, lines 24 & 64: "H13" should read --M13--

Column 8, line 64: "six" should read --mix--

Column 10, line 67: "a" should read --are--

Column 11, line 2: "a" should read --and--

UNITED STATES PATENT AND TRADEMARK OFFICE
CERTIFICATE OF CORRECTION

PATENT NO. : 5,670,630
DATED : September 23, 1997
INVENTOR(S) : Gregory P. Thill It is certified that error appears in the above-identified patent and that said Letters Patent are hereby corrected as shown below:

Column 11, line 43: "syntha" should read --synthase--

Column 11, line 49: "my" should read --may--

Column 11, line 58: after "insertable" insert --DNA--

Column 17, line 26: "Xb" should read --XbaI--

Column 18, line 27: "$MgCl_2$, $ZnCl_2$" should read --$MgCl_2$, 100 $\mu M$ $ZnCl_2$--

Column 18, line 49: "100 mM" should read --100 $\mu M$--

Column 18, line 59: "bad" should read --had--

Column 19, line 8: "beat" should read --heat--

UNITED STATES PATENT AND TRADEMARK OFFICE
CERTIFICATE OF CORRECTION

PATENT NO. : 5,670,630
DATED : September 23, 1997
INVENTOR(S) : Gregory P. Thill Page 3 of 3

It is certified that error appears in the above-identified patent and that said Letters Patent are hereby corrected as shown below:

Column 20, line 66: "ml" should read --10mM--

Column 22, line 6: "100M" should read --100 µM--

Column 25, line 10: "rising" should read --using--

Column 25, line 25: "NaCl $_1$, $_{0.1}$ %" should read --NaCl, 0.1%--

Column 25, line 27: "7.5)]" should read --7.5]--

Column 26, line 27: "AUSTRIA" should read --AUSRIA--

Signed and Sealed this

Fifteenth Day of May, 2001

Attest:

NICHOLAS P. GODICI

Attesting Officer

Acting Director of the United States Patent and Trademark Office